US009150584B2

(12) United States Patent
Moriarty

(10) Patent No.: US 9,150,584 B2
(45) Date of Patent: Oct. 6, 2015

(54) INDOLE AND BENZOFURAN FUSED ISOQUINUCLIDENE DERIVATIVES AND PROCESSES FOR PREPARING THEM

(71) Applicant: DemeRx, Inc., Miami, FL (US)

(72) Inventor: Robert M. Moriarty, Michiana Shores, IN (US)

(73) Assignee: DEMERX, INC., Miami, FL (US)

( * ) Notice: Subject to any disclaimer, the term of this patent is extended or adjusted under 35 U.S.C. 154(b) by 125 days.

(21) Appl. No.: 13/749,593

(22) Filed: Jan. 24, 2013

(65) Prior Publication Data

US 2013/0211074 A1     Aug. 15, 2013

Related U.S. Application Data

(60) Provisional application No. 61/590,740, filed on Jan. 25, 2012, provisional application No. 61/591,258, filed on Jan. 26, 2012.

(51) Int. Cl.
*C07D 491/22* (2006.01)
*C07D 471/22* (2006.01)

(52) U.S. Cl.
CPC ............ *C07D 491/22* (2013.01); *C07D 471/22* (2013.01)

(58) Field of Classification Search
CPC .................................................... C07D 491/22
USPC ....................................................... 540/579
See application file for complete search history.

(56) References Cited

U.S. PATENT DOCUMENTS

| | | | |
|---|---|---|---|
| 2,813,873 A | 11/1957 | Janot et al. |
| 3,516,989 A | 6/1970 | Sallay |
| 3,557,126 A | 1/1971 | Sallay, S. I. |
| 3,574,220 A | 4/1971 | Sallay |
| 3,639,408 A | 2/1972 | Nagata et al. |
| 3,715,361 A | 2/1973 | Epstein et al. |
| 3,875,011 A | 4/1975 | Rubenstein et al. |
| 3,885,027 A | 5/1975 | Shaw et al. |
| 4,107,288 A | 8/1978 | Oppenheim et al. |
| 4,272,541 A | 6/1981 | Kotick et al. |
| 4,375,414 A | 3/1983 | Strahilevitz |
| 4,444,758 A | 4/1984 | Scherschlicht et al. |
| 4,462,941 A | 7/1984 | Lee et al. |
| 4,464,378 A | 8/1984 | Hussain |
| 4,499,096 A | 2/1985 | Lotsof |
| 4,573,995 A | 3/1986 | Chen et al. |
| 4,587,243 A | 5/1986 | Lotsof |
| 4,604,365 A | 8/1986 | O'Neill et al. |
| 4,620,977 A | 11/1986 | Strahilevitz |
| 4,626,539 A | 12/1986 | Aungst et al. |
| 4,661,492 A | 4/1987 | Lewis et al. |
| 4,668,232 A | 5/1987 | Cordes et al. |
| 4,806,341 A | 2/1989 | Chien et al. |
| 4,857,523 A | 8/1989 | Lotsof |
| 5,026,697 A | 6/1991 | Lotsof |
| 5,075,341 A | 12/1991 | Mendelson et al. |
| 5,145,684 A | 9/1992 | Liversidge et al. |
| 5,149,538 A | 9/1992 | Granger et al. |
| 5,152,994 A | 10/1992 | Lotsof |
| 5,283,247 A | 2/1994 | Dwivedi et al. |
| 5,290,784 A | 3/1994 | Qu et al. |
| 5,316,759 A | 5/1994 | Rose et al. |
| 5,382,657 A | 1/1995 | Karasiewicz et al. |
| 5,426,112 A | 6/1995 | Zagon et al. |
| 5,552,406 A | 9/1996 | Mendelson et al. |
| 5,574,052 A | 11/1996 | Rose et al. |
| 5,578,645 A | 11/1996 | Askanazi et al. |
| 5,580,876 A | 12/1996 | Crain et al. |
| 5,591,738 A | 1/1997 | Lotsof |
| 5,618,555 A | 4/1997 | Tokuda et al. |
| 5,703,101 A | 12/1997 | Rose et al. |
| 5,726,190 A | 3/1998 | Rose et al. |
| 5,760,044 A | 6/1998 | Archer |
| 5,861,422 A | 1/1999 | Rose et al. |
| 5,865,444 A | 2/1999 | Kempf et al. |
| 5,925,634 A | 7/1999 | Olney |
| 5,932,238 A | 8/1999 | Opitz |
| 5,935,975 A | 8/1999 | Rose et al. |
| 6,211,360 B1 | 4/2001 | Glick et al. |
| 6,291,675 B1 | 9/2001 | Coop et al. |
| 6,348,456 B1 | 2/2002 | Mash et al. |
| 6,451,806 B2 | 9/2002 | Farrar |
| 6,806,291 B1 | 10/2004 | Sunkel et al. |
| 6,864,271 B2 | 3/2005 | Bazan et al. |
| 7,220,737 B1 | 5/2007 | Mash |
| 7,754,710 B2 | 7/2010 | Mash |

(Continued)

FOREIGN PATENT DOCUMENTS

| | | |
|---|---|---|
| CA | 2039197 | 9/1995 |
| DE | 22 17 132 | 10/1972 |

(Continued)

OTHER PUBLICATIONS

Paul et al., Synthesis of New Series of Iboga Analogues, Tetrahedron Letters, vol. 52, No. 46, pp. 6166-6169, 2011.*
U.S. Appl. No. 13/165,639, filed Jun. 21, 2011, Mash, et al.
Al-Shabanah, et al. "Gastric Antiulcer and Cytoprotective Effects of Cathinone, a Psychoactive Alkaloid of Khat (Catha Edulis Forsk.) and Amphetamine in Rats", Regulatory Peptides, 1994, abstract only.
Ala-Hurula, et al. "Ergotamine Abuse: Results of Ergotamine Discontinuation, with Special Reference to the Plasma Concentrations", Cephalalgia, 2:4 1982, abstract only.
Ala-Hurula, et al. "Tolfenamic Acid and Ergotamine Abuse", Headache, 21:6, 1981, abstract only.

(Continued)

*Primary Examiner* — Brenda Coleman
(74) *Attorney, Agent, or Firm* — Foley & Lardner LLP

(57) ABSTRACT

Provided herein are indole and benzofuran fused isoquinuclidene derivatives. Also provided herein are processes, preferably enantioselective processes, for preparing such derivatives including processes for preparing (−) and (+) noribogaine or a salt thereof, in substantially enantiomerically pure forms.

7 Claims, 3 Drawing Sheets

(56) References Cited

U.S. PATENT DOCUMENTS

| | | | |
|---|---|---|---|
| 8,017,151 | B2 | 9/2011 | Batrakova et al. |
| 8,178,524 | B2 | 5/2012 | Mash |
| 8,362,007 | B1 | 1/2013 | Mash et al. |
| 8,637,648 | B1 | 1/2014 | Mash et al. |
| 8,741,891 | B1 | 6/2014 | Mash |
| 8,765,737 | B1 | 7/2014 | Mash et al. |
| 2006/0051317 | A1 | 3/2006 | Batrakova et al. |
| 2010/0311722 | A1 | 12/2010 | Mash |
| 2010/0311723 | A1 | 12/2010 | Mash |
| 2010/0311725 | A1 | 12/2010 | Mash |
| 2012/0083485 | A1 | 4/2012 | Mash |
| 2013/0131046 | A1 | 5/2013 | Moriarty et al. |
| 2013/0303756 | A1 | 11/2013 | Mash et al. |
| 2014/0113878 | A1 | 4/2014 | Mash et al. |

FOREIGN PATENT DOCUMENTS

| | | |
|---|---|---|
| GB | 0 841 697 | 7/1960 |
| GB | 0 924 042 | 4/1962 |
| GB | 1 256 914 | 12/1971 |
| GB | 1 378 348 | 12/1974 |
| GB | 2 271 059 | 4/1994 |
| JP | 04-221315 | 8/1992 |
| JP | 2010-229097 A | 10/2010 |
| JP | 2011-068587 A | 4/2011 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/03127 A1 | 2/1996 |
| WO | WO-97/20847 | 6/1997 |
| WO | WO-2012/012764 A1 | 1/2012 |

OTHER PUBLICATIONS

Alexander. "A Procedure for Drug Screening Without the Need to Transport Urines Use of Ion Exchange Papers and Hem Agglutination Inhibition", Clinical Toxicology, 9:3, 1976, abstract only.

Alim, et al. "Open-Label, Dose Run-Up Study of Diethylpropion in Initial Cocaine Abstinence", Clinical Neuropharmacology, 17:2, 1994, abstract only.

Almeida. "Use and Abuse of Alcohol and Drugs a Clinical Study of Certain Aspects of Their Interrelationship", Boletin de la Oficina Sanitaria Panamericana, 88:1, 1980, abstract only.

Azevedo, et al. "Adrenergic Nerve Degeneration Induced by Condensation Products of Adrenaline and Acetaldehyde," Naunyn-Schmiedeberg's Archives of Pharmacology, 300:2, 1977, abstract only.

Bagal, et al. "Modulation of Morphine-Induced Antinociception by Ibogaine and Noribogaine", Brain Research, 741:1-2, 1996, pp. 258-262.

Bartlett, et al. "The Alkaloids of Tabernanthe iboga. Part IV. The Structures of Ibogamine, Ibogaine, Tabernanthine and Voacangine." Journal of the American Chemical Society, 80, 1958, pp. 126-136.

Batrakova. "Pluronic P85 Enhances the Delivery of Digoxin to the Brain: In Vitro and In Vivo Studies", The Journal of Pharmacology and Experimental Therapy, 296, 2001, pp. 551-557.

Beaubrun. "The Diagnosis and Management of Acute Psychotic Reaction Due to Alcohol and Drugs", Caribbean Medical Journal, 36:1, 1975, abstract only.

Beck, et al. "Energy-Dependent Reduced Drug Binding as a Mechanism of Vinca Alkaloid Resistance in Human Leukemic Lymphoblasts", Molecular Pharmacology, 24:3, 1983, abstract only.

Benet, et al. "Pharmacokinetics: Biotransformation of Drugs." In Gilman et al. Goodman and Gilman's the Pharmacological Basis of Therapeutics, 1990, pp. 13-16.

Benoist, et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunology Immunotherapy, 30:5, abstract only.

Bert, et al. "Non-Amphetaminic Central Stimulation by Alkaloids from the Ibogaine and Vobasine Series", Planta Medicina, 54:3, 1988, abstract only.

Bhargava, et al. "Effects of ibogaine and noribogaine on the antinociceptive action of mu-, delta- and kappa-opioid receptor agonists in mice", Brain Research 752, 1997, pp. 234-238.

Blum, et al. "Peyote a Potential Ethnopharmacologic Agent for Alcoholism and Other Drug Dependencies Possible Biochemical Rationale", Clinical Toxicology, 11:4, 1977, abstract only.

Blum, et al. "Possible Role of Tetrahydroisoquinoline Alkaloids in Postalcohol Intoxication States", Annals of the New York Academy of Science, 273, 1, abstract only.

Blum, et al. "Putative Role of Isoquinoline Alkaloids in Alcoholism: A Link to Opiates", Alcoholism: Clinical and Experimental Research, 2:2, 1978, abstract only.

Brady, et al. "Analgesic Effects of Intraventricular Morphine and Enkephalins in Nondependent and Morphine-Dependent Rats," Journal of Pharmacology and Experimental Therapy, 222:1, 1982, abstract only.

Buchi, et al. "The total synthesis of iboga alkaloids," Jounal of the American Chemical Society, 88, 1966, pp. 3099-3109.

Bundgaard. "Design of Prodrugs: Bioreversible Derivatives for Various Functional Groups and Chemical Entities." Design of Prodrugs, 1-10, 1985.

Bussel, et al. "Isolated Thrombocytopenia in Patients Infected with HIV Treatment with Intravenous Gamma Globulin," American Journal of Hematology, 28:2, 1988, abstract only.

Caldwell, et al. "The Biochemical Pharmacology of Abused Drugs. III. Cannabis, Opiates, and Synthetic Narcotics," Clinical Pharmacological Therapy, 16:6, 1974, abstract only.

Cankat. "Pharmacological Aspects of Drug Induced Headache", Functional Neurology, 7:6, 1992, abstract only.

Cappendijk, et al. "The Inhibitory Effect of Norharman on Morphine Withdrawal Syndrome in Rats: Comparison with Ibogaine." Behavioural Brain Research, 65, 1994, pp. 117-119.

Cappendijk, et al. "Inhibitory Effects of Ibogaine on Cocaine Self-Administration in Rats", European Journal of Pharmacology, 241:2-3, 1993, abstract only.

Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.

Cherny, et al., Opioid responsiveness of cancer pain syndromes caused by neuropathic or nociceptive mechanisms: a combined analysis of controlled, single-dose studies, Neurobiology 44, 1994, pp. 857-861.

Cheze, et al. "Determination of ibogaine and noribogaine in biological fluids and hair by LC-MS/MS after Tabernanthe iboga abuse", Forensic Science International, Elsevierscientific Publishers Ireland Ltd, IE, vol. 176, No. 1, Nov. 19, 2007, pp. 58-66.

Criel, et al. "Drug Dependent Red Cell Antibodies and Intravascular Haemolysis Occurring in Patients Treated with 9 Hydroxy-Methyl-Ellipticinium," British Journal of Haematology, 46:4, 1980, abstract only.

Damstrup, et al. "Retroperitoneal Fibrosis After Long-Term Daily Use of Ergotamine," International Urology and Nephrology, 18:3, 1986, abstract only.

Deecher, et al. "Mechanisms of Action of Ibogaine and Harmaline Congeners Based on Radioligand Binding Studies." Brain Research 571, 1992, pp. 242-247.

Diener, et al. "Analgesic-Induced Chronic Headache Long-Term Results of Withdrawal Therapy," Journal of Neurology, 236:1, 1989, abstract only.

Dierckx, et al. "Intraarterial Sodium Nitroprusside Infusion in the Treatment of Severe Ergotism," Clinical Neuropharmacology, 9:6, 1986, abstract only.

(56) References Cited

OTHER PUBLICATIONS

Dzoljic, et al. "Effect of Ibogaine on Naloxone-Precipitated Withdrawal Syndrome in Chronic Morphine-Dependent Rats," Archives Internationales de Pharmacodynamie et de Thérapie, 294, 1988, pp. 64-70.
Eberwine, et al. "Molecular Analysis of Cellular Responses to Opiate Use", Fidia Research Foundation Symposium Series 7 (Neurotransmitter Regulation of Gene Transcription) 1991, abstract only.
Elkind. "Drug Abuse and Headache", Medical Clinics of North America, 75:3, 1991, abstract only.
Evenson. "Developments in Therapeutic Drug Monitoring and Alkaloid Analysis", Federation Proceedings, 34:12, 1975, abstract only.
Faglia, et al. "Dihydroergocryptine in Management of Microprolactinomas," Journal of Clinical Endocrinology & Metabolism, 65:4 1987, abstract only.
Fairchild, et al. "Keynote Address: Multidrug Resistance: A Pleiotropic Response to Cytotoxic Drugs," International Journal of Radiation, Oncology, Biology, & Physics, 20:2, 1991, abstract only.
Finkle. "Phencyclidine Identification by Thin-Layer Chromatography. A Rapid Screening Procedure for Emergency Toxicology", American Journal of Clinical Pathology, 70:2, 1978, abstract only.
Fonne-Pfister, et al. "Xenobiotic and Endobiotic Inhibitors of Cytochrome P-450db1 Function, the Target of the Debrisoquine / Sparteine Type Polymorphism," Biochemical Pharmacology, 37:20, 1988, abstract only.
Frances, et al. "Effects of Ibogaine on Naloxone-Precipitated Withdrawal in Morphine-Dependent Mice", Fundamental Clininical Pharmacology, 6:8-9, 1992, abstract only.
Gabr, et al. "Changes in Absolute Amount of Alkaloids in Datura-Metel Treated with Certain Growth Regulators", Herba Pot, 21:2, 1975, abstract only.
Garcia, et al. Chronic pain states: pathophysiology and medical therapy, Seminars in Arthritis and Rheumatism, 27, 1997, pp. 1-16.
Gennaro. "Remington: The Science and Practice of Pharmacy", Mack Publishing Col., vol. II, 1995, pp. 1736 & 1814.
George, et al. "Palliative medicine", Postgraduate Medical Journal, vol. 69, 1993, pp. 426-449.
Gifford, et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41:4, 1992, abstract only.
Glick, et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657, 1994 pp. 14-22.
Glick, et al. "Effect of Ibogaine on Acute Signs of Morphine Withdrawal in Rats: Independence from Tremor", Neuropharmacology, 31:5, 1992, abstract only.
Glick, et al. "Effects of Aftereffects of Ibogaine on Morphine Self-Administration in Rats", European Journal of Pharmacology, 195:3, 1991, abstract only.
Glick, et al. "Ibogaine-like effects of noribogaine in rats", Brain Research, 713, 1996, pp. 294-297.
Glick, et al. "Local Effects of Ibogaine on Extracellular Levels of Dopamine and Its Metabolites in Nucleus Accumbens and Striatum: Interactions with D-Amphetamine", Brain Research, 628:1-2, 1993, abstract only.
Gold, et al. "Effect of Methadone Dosage on Clonidine Detoxification Efficacy", American Journal Psychiatry, 137:3, 1980, abstract only.
Gothoni. "Harmine-, Lon-954- and 5-Hydroxytryptophan-Induced Tremors in Rats Withdrawn from Ethanol", Acta Pharmacologica et Toxicologica, Copenhagen, DK, 57:1, 1985, abstract only.
Gross. "Effect of Ergot Alkaloids on Serum Prolactin in Non-Psychotic Organic Brain Syndrome of the Elderly", Experimental Aging Research, 5:4, 1979, abstract only.
Gunn. "Relations Between Chemical Constitution, Pharmacological Actions, and Therapeutic Uses, in the Harmine Group of Alkaloids." From the Pharmacological Laboratory, University of Oxford, 1935, pp. 379-396.
Haber, et al. "Tetrahydroisoquinolines—Endogenous Products After Chronic Alcohol Abuse", Pharmazie, 47:1, 1992, abstract only.
Halikas, et al. "Treatment of Crack Cocaine Use with Carbamazepine", American Journal of Drug and Alcohol Abuse, 18:1, 1992, abstract only.
Hanks. "Opioid-responsive and opioid-non-responsive pain in cancer," British Medical Bulletin 47, 1991, pp. 718-731.
Hardman, et al. "Principles of Therapeutics," in Goodman, et al (ed.), "Goodman & Gilman's the Pharmacological Basis of Therapeutics." 9th Ed., McGraw-Hill,1996, pp. 51, 57-58.
Harsing, et al. "Evidence that Ibogaine Releases Dopamine from the Cytoplasmic Pool in Isloated Mouse Striatum", Journal of Neural Transmission General Section, 96:3, 1994, abstract only.
Hearn, et al. "Identification and Quantitation of Ibogaine and an o-Demethylated Metabolite in Brain and Biological Fluids Using Gas Chromatography-Mass Spectrometry." Journal Analytical Toxicology, 19, 1995, pp. 427-434.
Heel al. "Buprenorphine: A Review of Its Pharmacological Properties and Therapeutic Efficacy", Drugs, 17:2, 1979, abstract only.
Hennessy et al., "Discovery of amniopiperidine-based Smac mimetics as IAP antagonists," Bioorg. Med. Chem. Lett., (2012), 22:1690-1694.
Henry, et al. "Reversible Cerebral Arteriopathy Associated with the Administration of Ergot Derivatives", Cephalalgia, 4:3, 1984, abstract only.
Ho, et al. "Metabolism of Harmaline in Rats." Biochemical Pharmacology vol. 20, 1971, pp. 1313-1319.
Hock et al., "Enantioselective Synthesis of (−)-(19R)-Ibogamin-19-ol," Helvetica Chimica Acta, (2006), 89:542-557.
Hoes. "Clinical Criteria for the Selection of Anxiolytics", Tijdschrift voor Therapie Geneesmiddel en Onderzoek, 9:9, 1984, abstract only.
Holbrook. "Nicotine Addiction." in Isselbacher et al. (ed.), "Harrison's Principals of Internal Medicine" 13th Ed., McGraw-Hill Inc., 1994, 2433-2437.
Holzner, et al. "The Neuroleptic Sleeping Course in Chronic Headache", Therapiewoche, 35/36: 1985 abstract only.
Huang, et al. "Cytotoxicity and Sister Chromatid Exchanges Induced in Vitro by Six Anticancer Drugs Developed in the People's Republic of China", Journal of the National Cancer Institute, 71:4, 1983, abstract only.
Hubens, et al. "Chronic Intake of a Hydrogenated Ergot Alkaloid Causing Peripheral Vascular Ischemia—A Case Report", Journal of Vascular Surgery, 21:4, 1987, abstract only.
Huffman, et al. "A Formal Synthesis of (±)-Ibogamine," Journal of Organic Chemistry, vol. 50, 1985, pp.1460-1464.
Isler. "Treatment of Headache", Schweizerische Medizinische Wochenschrift, 114:35, 1984, abstract only.
Jaffe. "Drug Addiction and Drug Abuse." In Goodman & Gilman (ed.)"The Pharmacological Basis of Therapeutics," 8th Ed., Pergamon Press, 1990, pp. 520-523 & pp. 559-568.
Jaffe. "Psychopharmacology and Opiate Dependence," U.S. Public Health Services Publication, 1957-1967: pp. 1836. 1967.
James. "Linkers for solid phase organic synthesis," Tetrahedron, 55, 1999, pp. 4855-4946.
Jana et al., "Progress in the Synthesis of Iboga-alkaloids and their Congeners," Organic Preparation and Procedures International, (2011) 43:541-573.
Jana et al., "Synthesis of iboga alkaloids by Pd-catalyzed heteroannulation of 2-iodoaniline with an internal alkyne as the key step," Tetrahedron Letters, (2010), 51:1441-1443.
Jane, et al. "High-Performance Liquid Chromatographic Analysis of Basic Drugs on Silica Columns Using Non-Aqueous Ionic Eluents. II. Application of UV, Fluorescence and Electrochemical Oxidation detection", Journal of Chromatography, 323:2, 1985 abstract only.
Jansen, et al. "Ethnopharmacology of Kratom the Mitragyna Alkaloids", Journal of Ethnopharmacology, 23:1, 1988, abstract only.
Janzen. "History of Use of Psychotropic Drugs in Central Africa," Psychotropes, 1/2: 1983, abstract only.

(56) References Cited

OTHER PUBLICATIONS

Justins. "Management strategies for chronic pain," Annals of the Rheumatic Diseases, vol. 55, 1996, pp. 588-596.
Kalix. "Khat: A Plant with Amphetamine Effects," Journal of Substance Abuse Treatment, 5:3, 1988, abstract only.
Kalix. "Pharmacological Properties of the Stimulant Khat", Pharmacological Therapy, 48:3, 1990, abstract only.
Keefner. "A Gas Chromatography-Mass Spectrometry (GCMS) Method for Ibogaine", Society for Neuroscience Abstracts, 19:1-3, 1993, abstract only.
Keller, et al. "Modulation of Neopterin Release by Human Kupffer Cells in Culture: Possible Implication in Clinical Monitoring of HIV-Seropositive Subjects", Cells Hepatic Sinusoid, 3: 1991, abstract only.
Knoll. "Azidomorphines and Homopyrimidazols: A New Approach to the Ideal Analgetic," ACTA Physiologica et Pharmacologica Bulgarica, 3:2, 1977, abstract only.
Knoll. "Azidomorphines: A New Family of Potent Analgesics with Low Dependence Capacity," Progress in Neuro-Psychopharmacology and Biological Psychiatry, 3:1-3, 1979, abstract only.
Koch, et al. "Drug-Induced Liver Injury in Liver Biopsies of the Years 1981 and 1983, their Prevalence and Type of Presentation", Pathology, Research and Practice, 179: 1985, abstract only.
Konig. "Psychiatric Intensive Therapy After Acute Alkaloid Withdrawal Syndrome", Infusionsther Klin Ernahr, 6:1, 1979, abstract only.
Kornetsky. "Pharmacology Drugs Affecting Behavior." John Wiley & Sons, 1976, pp. 185-187.
Kostowski, et al. "The Effects of Some Hallucinogens on Aggressiveness of Mice and Rats" Pharmacology, 7, 1972, pp. 259-263.
Krug. "Cocaine Abuse: Historical, Epidemiologic, and Clinical Perspectives for Pediatricians", Advances in Pediatrics, 36: 1989, pp. 369-406.
Kuehne, et al. "Biomimetric syntheses of indole alkaloids. 11. Syntheses of .beta.-carboline and indoloazepine intermediates," Journal of Organic Chemistry, 50:7, 1985, pp. 919-924.
Kupers, et al. "Morphine differentially affects the sensory and affective pain ratings in neuorgenic and idiopathic forms of pain." Pain, 47, 1991, pp. 5-12.
Lakoski, et al. "Electrophysiologic Characterization of an Ibogaine Metabolite in Dorsal Raphe Nucleus and Hippocampus." Society for Neuroscience, 21:716, 1995, abstract only.
Larson-Prior, et al. "Electrophysiologic Characterization of an Ibogaine Metabolite in the Cerebellar Cortex." Society for Neuroscience, 21:716, 1995, abstract only.
Lemontt, et al. "Increase MDR Gene Expression and Decreased Drug Accumulation in Multidrug-Resistant Human Melanoma Cells", Cancer Research, 48:22, 1988, abstract only.
Leoni, et al. "Effect of Cocaine and Morphine on Neutral Endopeptidase Activity of Human Peripheral Blood Mononuclear Cells Cultures with Lectins," Cell Biochemistry and Function, 11:3, 1993, abstract only.
Lerida, et al. "Incidence of Morphine Withdrawal and Quasi-Abstinence Syndrome in a Model of Chronic Pain in the Rat," Neuroscience, 81:1-2, 1987, abstract only.
Lewis, et al. "Adverse Reactions and Interactions with .beta.-Adrenoceptor Blocking Drugs," Journal of Medical Toxicology, 1:5, 1986, abstract only.
Lewis, et al. "Narcotic Analgesics and Antagonists," Annual Review of Pharmacology, 11, 1971, abstract only.
Licht, et al. "Induction of Multiple-Drug Resistance During Anti-Neoplastic Chemotherapy In-Vitro," International Journal of Cancer, 49:4, 1991, abstract only.
Ling, et al. "Drugs of Abuse-Opiates", in Addtiction Medicine [Special Issue], Western Journal of Medicine, 152, 1990, pp. 565-572.
Low, et al. "Effects of Acronycine and Cytouchalasin B on the Division of Rat Leukemia Cells," Experimental Cell Research, 131:1, 1981, abstract only.
Ma, et al. "Inhibition of Respiratory Burst Activity in Alveolar Macrophages by Bisbenzylisoquinoline Alkaloids: Characterization of Drug-Cell Interaction", Experimental Lung Research, 18:6, 1992, abstract only.
Maisonneuve, et al. "Interactions of Ibogaine and D-Amphetamine: in vivio Microdialysis and Motor Behavior in Rats." Brain Research 579, 1992 pp. 87-92.
Maisonneuve, et al. "Acute and Prolonged Effects of Ibogaine on Brain Dopamine Metabolism and Morphine-Induced Locomotor Activity in Rats", Brain Research, 575:1, 1992, abstract only.
Maisonneuve, et al. "Interactions Between Ibogaine, a Potential Anti-Addictive Agent, and Morphine: an in Vivo Microdialysis Study," European Journal of Pharmacology, 199:1, 1991, abstract only.
Martellotta, et al. "Effects of the Calcium Antagonist Isradipine on Cocaine Intravenous Self-Administration in Rats", Psychopharmacologia, 113:3-4, 1994, abstract only.
Martin, et al. "Neuropathic Pain in Cancer Patients: Mechanisms, Syndromes, and Clinical Controversies," Journal of Pain and Symptom Management, 14:2, 1997, pp. 99-117.
Mash, et al. "Ibogaine in the Treatment of Heroin Withdrawal," The Alkaloids 56, 2001, pp. 1-17.
Mash, et al. "Ligand Binding Profiles of Ibogaine and its O-demethylated Metabolite Noribogaine: Implications for Developing Novel Multi-target Anti-addiction Agents." Society of Neurosciences, vol. 21, 1995 abstract only.
Mash, et al. "Preclinical screening of an ibogaie metabolite (noribogaine) on cocaine-induced hyperlocomotion and cocaine self-administration." Society of Neurosciences, vol. 22, 1996, abstract only.
Mash, et al. "Properties of Ibogaine and its Principle Metabolite (12-hydroxyibogamine) at the MK-801 binding site of the NMDA receptor complex," Neuroscience Letters, 192, 1995, pp. 53-56.
Mateer, et al. "Reversible Ipecac Myopathy," Archives of Neurology, 42:2, 1985, abstract only.
Matharu, et al. "Preformulation and Development of Ibogaine Injection for the Treatment of Drug Abuse," Pharmaceutical Research, 10: 1993, abstract only.
Mattingly, et al. "Selective Antagonism of Dopamine D Sub 1 and D Sub 2 Receptors Does Not Block the Development of Behavioral Sensitization to Cocaine," Psychopharmacologia, 114:2, 1994, abstract only.
McNeish, et al. "The 5-HT Sub 3 Antagonist Zacopride Attenuates Cocaine-Induced Increases in Extracellular Dopamine in Rat Nucleus Accumbens," Pharmacology, Biochemistry, and Behavior, 45:4, 1993, abstract only.
Melchior, et al. "Preference for Alcohol Evoked by Tetra Hydro Papaveroline Chronically Infused in the Cerebral Ventricle of the Rat," Pharmacol Biochem Behav, 7:1, 1977, abstract only.
Mendelson & Mello "Cocaine and Other Commonly Abused Drugs." In Isselbacher et al. (ed.), "Harrison's Principals of Internal Medicine." 13th Ed., McGraw-Hill Inc., 1994, pp. 2429-2433.
Menzies, et al. "Gangrene of the Small Bowel: A Complication of Methysergide Therapy," Australian and New Zealand Journal of Surgery, 52:5, 1982, abstract only.
Metelitsa. "Pharmacological Agents in Controlling Smoking," Biull Vsesoiuznogo Kardiol Nauchn Tsentra, 10:1, 1987, abstract only.
Millan. "k-Opioid Receptors and Analgesia," Trendes in Pharmacologicla Sciences, 11, 1990, pp. 70-76.
Mizuhashi, et al. "Antitumor Activities of IKP-104 A 4-1H Pyridizinone Derivative on Cultured and Implanted Tumors," Japanese Journal of Cancer Research, 81:12, 1990, abstract only.
Moisan et al., "Formal Synthesis of (+)-Catharanthine," Angew. Chem. Int. Ed., (2006), 45:5334-5336.
Montefiori, et al. "In Vitro Evaluation of Mismatched Double-Stranded RNA (Ampligen) for Combination Therapy in the Treatment of Acquired Immunodeficiency Syndrome,"AIDS Research and Human Retroviruses, 5:2, 1989, abstract only.
Mulamba, et al. "Alkaloids from Tabernathe Pubescens," Journal of Natural Products, vol. 44:2, 1981, pp. 184-189.
Naranjo. "Ibogaine in psychotherapy: psychoanalysis according to Naranjo", part IV, pp. 1-2. http://www.nettuno.it/fiera/electric.italy/bwitif.html (1969).

(56) References Cited

OTHER PUBLICATIONS

Nishiyama, et al. "Expression of the Multidrug Transporter, P-Glycoproteiin, in Renal and Transitional Cell Carcinomas," Cancer, 71:11, 1993, pp. 3611-3619.
Nooter, et al. "Multidrug Resistance (MDR) Genes in Haematological Malignancies,"Cytotechnology, 12:1-3, 1993, abstract only.
Nunn-Thompson, et al. "Pharmacotherapy for Making Cessation", Clin Pharm, 8:10, 1989, abstract only.
Obach, et al., "Cythochrome P4502D6 Catalyzes the O-Demethylation of the Psychoactive Alkaloid Ibogaine to 12-Hydroxyibogamine," Drug Metabolism and Disposition 26:8, 1998, pp. 764-768.
O'Hearn, et al. "Degenration of Prukinje Cells in Parasagittal Zones of the Cerebellar Vermis After Treatment with Ibogaine of Harmaline," Neuroscience, 55:2, 1993, abstract only.
O'Hearn, et al. "Ibogaine Induces Glial Activation in Parasagittal Zones of the Cerebellum," Neuroreport, 4:3, 1993, abstract only.
Pablo, et al, "Noribogaine Stimulates Naloxone-Sensitive[35S]GTPgammaS Binding," NeuroReport, 9, 1998, pp. 109-114. (Website Publication Date of Dec. 20, 1997.).
Pacifici, et al. "Immunological Effect of Cocaine and Host Resistance in Mice," International Journal of Immunotherapy, 8:2, 1992, abstract only.
Palyi. "Survivial Responses to New Cytostatic Hexitols of P388 Mouse and K562 Leukemia Cells in Vitro," Cancer Treatment Reports, 70:2, 1986, abstract only.
Pantazis, et al. "Efficacy of Camptothecin Congeners in the Treatment of Human Breast Carcinoma Xenografts," Oncology Research, 5:8, 1994, abstract only.
PCT International Search Report and Written Opinion dated May 14, 2013 in related PCT Patent Application No. PCT/US2013/022797.
PCT International Search Report and Written Opinion dated May 31, 2013 in related PCT Patent Application No. PCT/US2013/023017.
Pehek. "Effects of Cathinone and Amphetamine on the Neurochemistry of Dopamine in Vivo," Neuropharmacology, 29:12, 1990, abstract only.
Perera, et al. "Tertiary Indole Alkaloids of Tabernaemontana Dichotoma Seeds," Planta Medica, 49:1, 1983, abstract only.
Perrin. "Clinical Pharmacokinetics of Ergotamine in Migraine and Cluster Headache," Clinical Pharmacokinetics, 10:4, 1985, abstract only.
Popik, et al. "NMDA Antagonist Properties of the pUtative Antiaddictive Drug, Ibogaine," Journal of Pharmaceutical and Experimental Therapeutics, 275:2, 1995, pp. 753-760.
Popik, et al. "The Putative Anti-Addictive Drug Ibogaine is a Competitive Inhibitor of (SUP 3 H) Binding to the NMDA Receptor Complex", Psychopharmacologia, 114:4, 1994, abstract only.
Popik, et al. "100 Years of Ibogaine: Neurochemical and Pharmacological Actions of a Putative anti-addictive Drug," Pharmacological Reviews 47:2, 1995, pp. 235-253.
Pulvirenti, et al. "Lisuride Reduces Intravenous Cocaine Self-Administration in Rats,"Pharmacology, Biochemistry and Behavior, 47:4, 1994, abstract only.
Qiu, et al. "The Influence of Chronic Nicotine Treatment on Stress-Induces Gastric Ulceration and Emptying Rate in Rats," Experientia, 48:4, 1992 abstract only.
Radouco-Thomas, et al. "Adverse effects to Psychotomimetics. Proposition of a Psychopharmacological Classification." Pharmacologie, Toxicologie, et abus des psychotomimetiques (hallucinogens), 109, 1924, abstract only.
Rezvani, et al. "Noribogaine, a Primary Ibogaine Metabolite, Reduces Alcohol Intake in P And Fawn-Hooded Rats." RSA Annual Scientific Meeting, 1995, abstract only.
Rezvani, et al. "Reduction of Alcohol Intake in Alcohol Preferring Fawn-hooded and P Rats by Noribogaine, the Primary Metabolite of Ibogaine." NIDA Monograph Series 162:281, 1996, Abstract only.
Ricceri, et al. "Postnatal cocaine Esposure Affects Neonatal Passive Avoidance Performance and Cholinergic Development in Rats," Pharmacology, Biochemistry and Behavior, 45:2, 1993, abstract only.
Rodriguez, et al. "Cocaine Adminstration Prior to Reactivation Facilitates Later Acquisition of an Avoidance Response in Rats," Psychopharmacologia, 112:2-3, 1993, abstract only.
Rosenmund, et al. "Ibogamin, Ibogain and Epiibogamin" Chemische Berichte, 108, 1975, pp. 1871-1895.
Sachs, et al. "Corneal Complications Associated with the Use of Crack Cocaine," Ophthalmology, 100:2, 1993, abstract only.
Salmoiraghi, et al. "Effects of LSD 25, BOL 148, Bufotenine, Mescaline and Ibogaine on the Potentiation of Hexobarbital Hypnosis Produced by Serotonin and Reserpine." Journal of Pharmacology and Experimental Therapeutics 120:1, 1957, pp. 20-25.
Samadi-Baboli, et al. "Preparation of Low Density Lipoprotein-9-Methoxy-Illipticin Complex and Its Cytotoxic Effect Against L1210 and P 388 Leukemic Cells in Vitro," European Journal of Cancer and Clinical Oncology , 25:2 1989 abstract only.
Saper et al. "Ergotamine Tartrate Dependency: Features and Possible Mechanisms", Clinical Neuropharmacology, 9:3, 1986, abstract only.
Schecter, et al. "Comparison of the Behavioral Effects of Ibogaine from Three Sources: Mediation of Discriminative Activity," European Journal of Pharmacology, 249:1, 1993, abstract only.
Schneider, et al. "Analysis of the Cardiovascular Action of Ibogaine Hydrochloride." Archives Internationales de Pharmacodynamie et de Thérapie, 110, 1957, pp. 92-102.
Schneider, et al. "Neuropharmacological Studies of Ibogaine: An Indole Alkaloid with Central Stimulant Properties." Annals of the New York Academy of Sciences, 66, 1957, pp. 765-776.
Schneider, et al., "Potentiation Action of Ibogaine on Morphine Analgesia" Experientia, 12:8, 1956, pp. 323-324.
Schnider, et al. "Use and Abuse of Analgesics in Tension-Type Headache," Cephalalgia, 14:2, 1994, abstract only.
Schuckit & Segal. "Opiod Drug Use." In Isselbacher et al. (ed.), "Harrison's Principals of Internal Medicine" 13th Ed., McGraw-Hill Inc., 1994, 2425-2429.
Schuckit. "Alcohol and Alcoholism." In Isselbacher et al. (ed.), "Harrison's Principals of Internal Medicine" 13th Ed., McGraw-Hill Inc., 1994, pp. 2420-2425.
Seeber, et al. "In Vivo Resistance Towards Anthracyclines, Etoposide, and Cis-Diamminedichloroplatinum(II)," Cancer Research, 42:11, 1982, abstract only.
Sehested, et al. "The Carboxylic Ionophore Monensin Inhibits Active Drug Efflux and Modulates In-Vitro Resistance in Daunorubicin Resistant Enrlich Ascites Tumor Cells," Biochemical Pharmacology, 37:17, 1988 abstract only.
Sershen, et al. "Ibogaine Antagonizes Cocaine-Induced Locomotor Stimulation in Mice," Life Sciences, 50:15, 1992, abstract only.
Sershen, et al. "Ibogaine Reduces Amphetamine-Induced Locomotor Stimulation in C57BL/6By Mice, but Stimulates Locomotor Activity in Rats," Life Sciences, 51:13, 1992, abstract only.
Sershen, et al. "Ibogaine Reduces Preference for Cocaine Consumption in C57BL/6By Mice,"Pharmacology Biochemistry and Behavior, 47:1, 1994, abstract only.
Shen, et al. "Antagonists at Excitatory Opioid Receptors on Sensory Neurons in Culture Increase Potency and Specificity of Opiate Analgesics and Attenuate Development of Tolerance/ Dependence," Brain Research, 636:2, 1994, abstract only.
Sheppard. "A Preliminary Investigation of Ibogaine: Case Reports and Recommendations for Further Study." Journal of Substance Abuse Treatment, 11:4, 1994, abstract only.
Shir, et al. "Neuropathic pain unrelieved by morphine, alleviated by haloperidol," Harefuah 118:8, 1990, abstract only.
Shook, et al. "A Cyclic Somatostatin Analog that Precipitates Withdrawal in Morphine-Dependent Mice," NIDA Residential Monographs, 76, 1987, abstract only.
Sinkula, et al. "Rationale for Design for Biologically Reversible Drug Derivatives: Prodrugs." Journal of Pharmaceutical Sciences, 64:2, 1975, pp. 181-210.
Slotkin, et al. "A Model of Harmine Metabolism in the Rat." The Journal of Pharmacology and Experimental Therapeutics, 174:3, 1970, pp. 456-462.
Slotkin, et al. "Blood Levels and Urinary Excretion of Harmine and its Metabolites in Man and Rats."The Journal of Pharmacology and Experimental Therapeutics, 173:1, 1970, pp. 26-30.

(56) References Cited

OTHER PUBLICATIONS

Slotkin, et al. "Urinary Metabolites of Harmine in the Rat and their Inhibition of Monoamine Oxidase."Biochemical Pharmacology, 19, 1970, pp. 125-131.
Sloviter, et al. "A Common Mechanism of Lysergic Acid, Indolealkylamine and Phenethylamine Hallucinogens: Serotonergic Mediation of Behavioral Effects in Rats." Journal of Pharmacological Experimental Therapy, 214:2, 1980, pp. 231-238.
Smith. "Interaction of Biogenic Amines with Ethanol," Advances in Experimental Medicine and Biology, 56, 1975, abstract only.
Solinas, et al. "Solid-Supported Reagents and Catch-and-Release Techniques in Organic Synthesis", Synthesis 2007:16, 2007, pp. 2409-2453.
Stella. "Pro-drugs as Novel Drug Delivery Systems", ed. Higuchi, T. et al., American Chemical Society, Washington D.C., 1975, pp. 1-49.
Stella. "Pro-drugs: An Overview and Definition." Prodrugs as Novel Drug Delivery System. ACS Symposium Series: 1975, pp. 1-115.
Sugiyama, et al. "Quantitative Analysis of Cell-Kill Effects of Anticancer Drugs: Consideration of Both In Vitro and In Vivo Expreimental Systems." Gan to Kagaku Ryoho, 14:12, 1987, abstract only.
Tarnower, et al., "Ergotism Masquerading as Arteritis," Postgradate Medicine, 85:1, 1989, abstract only.
Teoh, et al. "Buprenorphine Effects on Morphine- and Cocaine-Induced Subjective Responses by Drug-Dependent Men," Journal of Clinical Psychopharmacology, 14:1, 1994, abstract only.
Tfelt-Hansen, et al. "Nitroglycerin for Ergotism. Experimental Studies in Vitro and in Migraine Patients and Treatment of an Overt Case," European Journal of Clinical Pharmacology, 22:2, 1982, abstract only.
Torrenegra, et al. "Alkaloids of stemmadenia grandiflora", Phytochemistry, 27:6, 1988, pp. 1843-1848.
Tsuruo. "Multidrug Resistance: A Transport System of Antitumor Agents and Xenobiotics," Princess Takamatsu Symp, 21, 1990, abstract only.
Uldry, et al. "Cerebrovascular Accidents in Relation to Drug Consumption or Drug Abuse," Schweizerische Rundschau Fur Medizin Praxis, 78:23, 1989, abstract only.
Valadez, et al. "Persistence of the Ability of Amphetamine Preexposure to Facilitate Acquistion of Cocaine Self-Administration," Pharmacology, Biochemistry and Behavior, 47:1, 1994, abstract only.
Valencia, et al. "Obovatine, a New Bisindole Alkaloid from Stemmadenia Obovata," Journal of Natural Products, 58:1, 1995, pp. 134-137.
Vescovi, et al. "Successful Treatment of Opiate Withdrawal Using Lysine Acetylsalicylate," Current Therapeutic Research, Clinical and Experimental, 33:5, 1983, abstract only.
Villalba, et al. "Uses and Abuses of Ipecacuana Syrup", Farmacia Clinica, 9:1, 1992, abstract only.
Wells, et al. "Recognition and Treatment of Arterial Insufficiency from Cafergot," Journal of Vascular Surgury, 4:1, 1986, abstract only.
Whitaker, et al. "High Affinity 3H-Serotonin Binding to Caudate: Inhibition by Hallucinogenic and Serotonergic Drugs," Psychopharmacology 59, 1978, pp. 1-5.
Whitaker, et al. "Selective Labeling of Serotonin Receptors by d'(3H)Lysergic Acid Diethylamide in Calf Caudate." Proceedings of the National Academy of Sciences 75:12, 1978, pp. 5783-5787.
Whittaker, et al. "Recurrent Laryngeal Nerve Paralysis in Patients Receiving Vincristine and Vinblastine", British Medical Journal, 1:6071, 1977, abstract only.
Widler, et al. "Pharmacodynamics and Pharmacokinetics of Khat: a Controlled Study," Clinical Pharmacology Therapy, 55:5, 1994, abstract only.
Wildmann. "Heterocycles as Physiological Ligands for the Benzodiazepine Receptor and for Other Binding Sites", Pharmacology Residency, 21:6, 1989, abstract only.
Williams, et al. "The 'Alice in Wonderland' Experience Ergot Alkaloid Therapy for Prolactin-Secreting Pituitary Tumors," The Western Journal of Medicine, 138:3, 1983, abstract only.
Wishart, et al. "Is Multidrug Resistance Relevant in Breast Cancer," European Journal of Surgical Oncology, 17:5, 1991, abstract only.
Witt, et al. "Pharmacodynamic and Pharmacokinetic Characterization of Poly(Ethylene glycol) Conjugation to Met-Enkephalin Analog [D-Pen2,D-Pen5]-enkephalin (DPDPE)", Journal of Pharmcological and Experimental Therapy, 298:2, 2001 pp. 848-856.
Witt, et al. "Pluronic P85 Block Copolymer Enhances Opioid Pepetide Analgesia," Journal of Pharmcology and Experimental Therapy, 303:2, 2002, pp. 760-767.
Worz. "Effects and Risks of Psychotropic and Analgesic Combinations," American Journal of Medicine, 75:5A, 1983, abstract only.
Zetler et al. "Pharmacokinetics in the Rat of the Hallucinogenic Alkaloids Harmine and Harmaline." Naunyn-Schmiedeberg's Arch. Pharmacol. 285, 1974, pp. 273-292.
Zetler, et al. "Cerebral Pharmacokinetics of Tremor-Producing Harmala and Iboga Alkaloids" Pharmacology, 7:4, 1972, pp. 237-248.
International Search Report and Written Opinion dated Feb. 25, 2013, in related PCT Application No. PCT/US2012/022787.
Kubiliene, et al., "Acute Toxicity of ibogaine and noribogaine," Medicina (Kaunas), (2008), 44(12):984-988.
White and Choi, Catalyzed Asymmetric Diels-Alder Reactions of Benzoquinone, Total Synthesis of (−)-Ibogamine. Helvetica Chimica Acta, vol. 85, 4306-4327, 2002.
Baxter et al., Model Studies Probing the Amino-Claisen Rearrangement Approach to Hydroisoquinoline Synthesis, Development of Methods for Stereocontrolled Introduction of Reserpine E Ring Type Functionality, J Org Chem 1989, 54, 2893-2904.
Final Office Action on U.S. Appl. No. 13/749,592 dated Apr. 1, 2015. 9 pages.

\* cited by examiner

INDOLE AND BENZOFURAN FUSED ISOQUINUCLIDENE DERIVATIVES AND PROCESSES FOR PREPARING THEM

CROSS REFERENCE TO RELATED APPLICATION

This application claims the benefit under 35 U.S.C. 119(e) of U.S. Provisional Application Ser. Nos. 61/590,740 filed Jan. 25, 2012 and 61/591,258 filed Jan. 26, 2012 and each of which is hereby incorporated by reference into this application in its entirety.

FIELD OF THE INVENTION

Provided herein are indole and benzofuran fused isoquinuclidene derivatives, and processes, preferably enantioselective processes, for preparing such derivatives including processes for preparing (−) and (+) noribogaine, in substantially enantiomerically pure forms. In certain aspects, the processes provided herein employ the novel isoquinuclidene, R,R 7-oxo-2-azabicyclo[2.2.2]oct-5-ene, or a protected derivative thereof (see, U.S. application No. 61/741,798, which is incorporated herein in its entirety by reference). In other aspects, this invention provides (−) or (+) noribogaine or a salt, preferably a pharmaceutically acceptable salt, of each thereof, preferably in a substantially enantiomerically pure form, prepared according to the processes provided herein, and also provides pharmaceutical compositions comprising (−) noribogaine or a salt thereof thus prepared.

STATE OF THE ART

Noribogaine is a well known compound whose structure combines the features, for example, of tryptamine, and isoquinuclidene. The naturally occurring enantiomer of noribogaine can be depicted by the following formula:

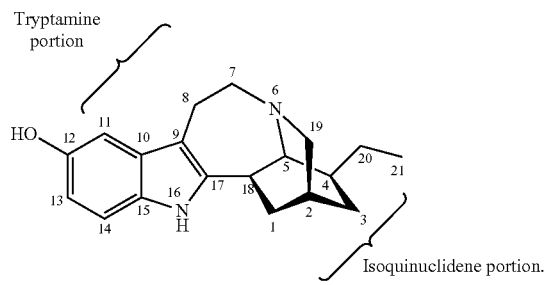

This enantiomer of noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737). Both of these patents are incorporated herein by reference in their entirety.

Synthesizing compounds to include the isoquinuclidene moiety, especially in a substantially enantiomerically pure form is a challenging task. Heretofore, Iboga alkaloids, such as ibogaine:

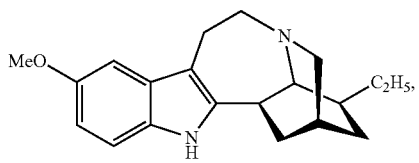

were conventionally prepared from one of its naturally occurring precursors such as voacangine:

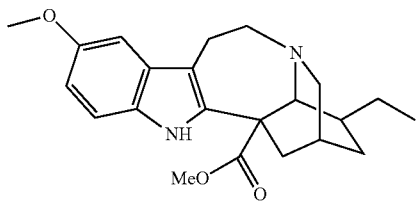 [SMILES: CCC1CC2CN3CCc4c([nH]c5ccc(OC)cc45)C(C(=O)OC)(C2)C13]

or isolated from plant sources. The naturally occurring enantiomer of noribogaine is prepared by O-demethylation of naturally occurring ibogaine or prepared by decarboxylation and O-demethylation of naturally occurring voacangine. Voacangine and Ibogaine are obtained from plants where both the supply is limited and the quality of the supply is unpredictable.

SUMMARY OF THE INVENTION

Provided herein are indole and benzofuran fused isoquinuclidene derivatives, and processes, preferably enantioselective processes, for preparing such derivatives including processes for preparing (−) or (+) noribogaine or a salt thereof, in substantially enantiomerically pure forms.

In certain aspects, the processes provided herein employ the novel 1R,4R 7-oxo-2-azabicyclo[2.2.2]oct-5-ene or a protected derivative thereof.

In another aspect, this invention provides (−) noribogaine or a salt, preferably a pharmaceutically acceptable salt, thereof, preferably in a substantially enantiomerically pure form, prepared according to the processes provided herein. In another aspect, this invention provides a composition comprising the (−) noribogaine or a pharmaceutically acceptable salt thereof and at least one pharmaceutically acceptable excipient.

This invention also provides processes for preparing (+) noribogaine.

As used herein, "pharmaceutically acceptable" refers to a safe and non-toxic composition, which is suitable for in vivo, preferably for human administration. Pharmaceutically acceptable salts or excipients are well known to the skilled artisan.

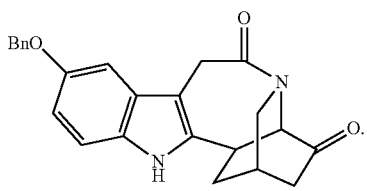

Compound 3

Figure 2:
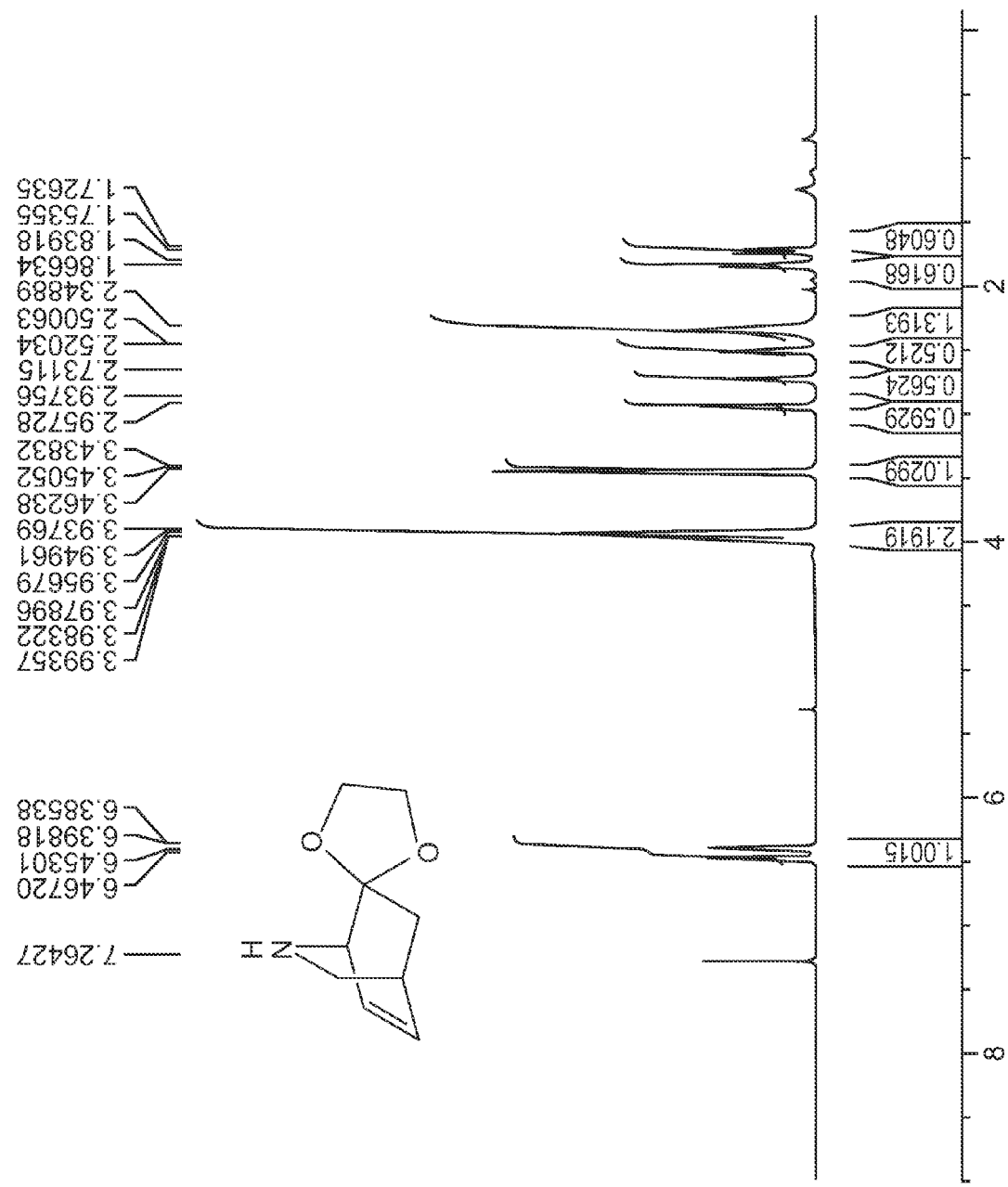

FIG. 2 illustrates a $^1$H-NMR spectrum in CDCl$_3$ of compound 1:

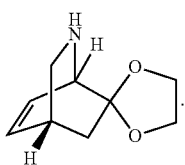

Compound 1

Figure 3:
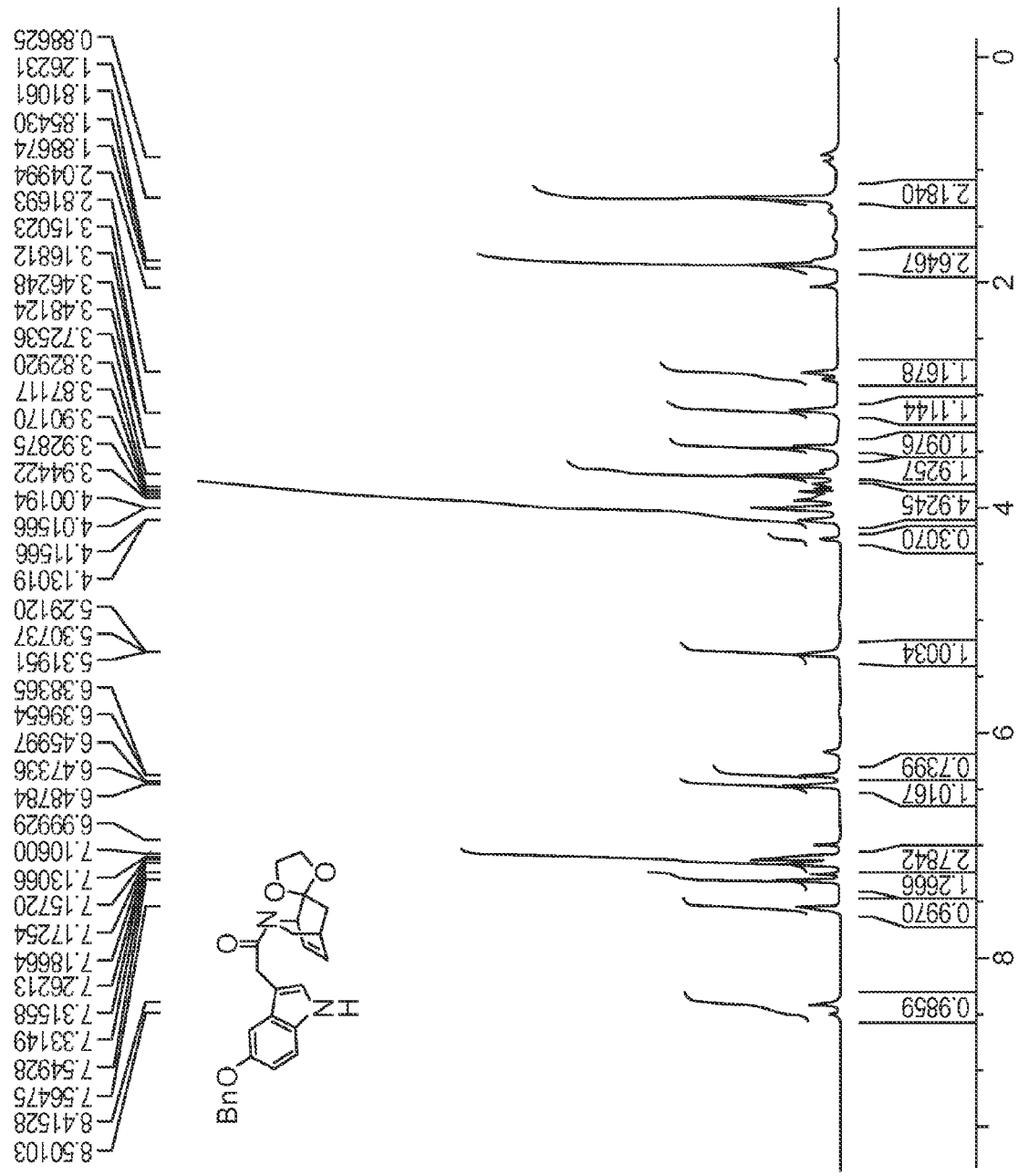

FIG. 3 illustrates a $^1$H-NMR spectrum in CDCl$_3$ of compound 2:

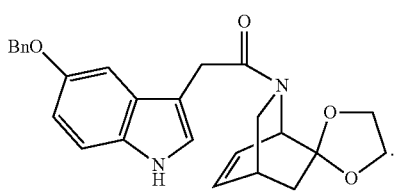

Compound 2

DETAILED DESCRIPTION OF THE INVENTION

Provided herein are indole and benzofuran fused isoquinuclidene derivatives, and processes, preferably enantioselective processes, for preparing such derivatives including processes for preparing (−) and (+) noribogaine or a salt of each thereof, in substantially enantiomerically pure forms. Before this invention is described in greater detail, the following terms will be defined.

As used herein and in the appended claims, the singular forms "a", "an", and "the" include plural referents unless the context clearly dictates otherwise. Thus, for example, reference to "a salt" includes a plurality of such salts.

DEFINITIONS

As used herein, "alkenyl" refers to hydrocarbyl groups having from 2 to 10 carbon atoms and at least one and up to 3 carbon carbon double bonds. Examples of alkenyl include vinyl, allyl, dimethyl allyl, and the like.

As used herein, "alkoxy" refers to —O-alkyl.

As used herein, "alkyl" refers to hydrocarbyl groups having from 1 to 10 carbon atoms, more preferably 1 to 6 carbon atoms, and still more preferably 1-4 carbon atoms. The alkyl group may contain linear or branched carbon chains. This term is exemplified by groups such as methyl, ethyl, n-propyl, iso-propyl, n-butyl, t-butyl, n-pentyl, n-decyl and the like.

As used herein, "alkynyl" refers to hydrocarbyl groups having from 2 to 10 carbon atoms and at least one and up to 2 carbon carbon triple bonds. Examples of alkynyl include ethynyl, propargyl, dimethylpropargyl, and the like.

As used herein, "amino" refers to —NR$^x$R$^y$ wherein each R$^x$ and R$^y$ independently is hydrogen, C$_1$-C$_6$ alkyl, C$_2$-C$_6$ alkenyl, C$_2$-C$_6$ alkynyl, C$_6$-C$_{10}$ aryl, C$_3$-C$_8$ cycloalkyl, C$_2$-C$_{10}$ heteroaryl, or C$_3$-C$_8$ heterocyclyl, or R$^x$ and R$^y$ together with the nitrogen atom they are bonded to form a 5-10 membered heterocyclyl ring containing 1-2 nitrogen and/or oxygen atoms, which heterocyclyl ring is optionally substituted with 1-3, preferably, 1-2, or more preferably, a single, C$_1$-C$_3$ alkyl group.

As used herein, "aryl" refers to an aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom.

As used herein, "base" refers to a compound that can accept a proton or donate a lone electron pair. Examples of bases include, alkali (OH), carbonate, bicarbonate, alkoxides (alkyl-O(−)), hydrides (alkali metal hydrides and CaH$_2$), amides (NH$_2$(−), R$^b$NH(−), or (R$^b$)$_2$N(−), wherein R$^b$ is alkyl or 2 R$^b$s together with the nitrogen form a 5-6 membered ring), and neutral nitrogen containing bases such as (R$^b$)$_3$N, pyridine, 4-N,N-dialkylpyridine, and the like. As used herein nucleophilic bases refer to preferably neutral nitrogen containing bases that can catalyze the addition of an acyl halide or a sulfonyl halide (such as R$^b$COX or R$^b$SO$_2$X) to an —OH, —NH$_2$, or an —NHR$^b$ group. Preferred examples include, 4-N,N-dialkylpyridines.

As used herein, a "Bronsted acid" refers to a compound that can donate a proton.

As used herein, the term "chlorinated solvent" refers to chlorinated methane and ethane, which are preferably trichlorinated, and more preferably dichlorinated. Yet more preferably, the chlorinated solvent is dichloromethane.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, "cycloalkyl" refers to cyclic hydrocarbyl groups of from 3 to 10 carbon atoms having single or multiple condensed rings, which condensed rings may be aromatic or contain a heteroatom, provided that the point of attachment is at a cycloalkyl carbon atom. Cycloalkyl includes, by way of example, adamantyl, cyclopropyl, cyclobutyl, cyclopentyl, cyclooctyl and the like. Cycloalkyl rings are preferably saturated, though, cycloalkyl rings including 1-2 carbon carbon double bonds are also contemplated provided that the ring is not aromatic.

As used herein, "C" refers to a group having x carbon atoms, wherein x is an integer, for example, C$_4$ alkyl refers to an alkyl group having 4 carbon atoms.

As used herein, "ee" refers to enantiomeric excess and is expressed as (e$^1$-e$^2$) % where e$^1$ and e$^2$ are the two enantiomers. For example, if the % of e$^1$ is 95 and the % of e$^2$ is 5, then the e$^1$ enantiomer is present in an ee of 90%. The ee of an enantiomer in a mixture of enantiomers is determined following various methods well known to the skilled artisan, such as using chiral lanthanide based nuclear magnetic resonance shift reagents, forming derivatives with chiral compounds such as chiral hydroxyacids, amino acids, and the like. Various physical measurements such as circular dichroism, optical rotation, etc. are also useful in determining the ee of a mixture of enantiomers.

As used herein, "deprotection condition" refers to reaction conditions that transform a phenolic ether to the corresponding phenol and includes reacting with various Lewis acids such as $BBr_3$, and when the alkyl group in the ether is a methyl group containing at least one phenyl or substituted phenyl group, reacting under hydrogenation conditions.

As used herein, $—CO_2H$ "ester" refers to $—CO_2R^E$ wherein $R^E$ is selected from the group consisting of $C_6$-$C_{10}$ aryl and $C_1$-$C_6$ alkyl optionally substituted with 1-3 $C_6$-$C_{10}$ aryl groups.

As used herein "Fischer indole synthesis condition" refers to reaction conditions for reacting phenylhydrazine with a ketone containing at least one α-methylene group and an acid to provide an indole derivative. Bronsted acids such as HCl, $H_2SO_4$, polyphosphoric acid and p-toluenesulfonic acid are useful, as are Lewis acids such as boron trifluoride, zinc chloride, iron chloride, and aluminum chloride.

As used herein, "fluoroalkyl" refers to an alkyl group substituted with up to 5, or preferably up to 3 fluoro groups.

As used herein, "halo" refers to F, Cl, Br, or I.

As used herein, "heteroaryl" refers to an aromatic group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—), provided that the ring has at least 5 ring atoms and up to 14, or preferably from 5-10, ring atoms. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Examples of heteroaryls include pyridyl, pyrrolyl, indolyl, thiophenyl, furyl, and the like.

As used herein, "heterocyclyl" or heterocycle refers to a cycloalkyl group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—), provided that the ring has at least 3 and up to 14, or preferably from 5-10 ring atoms. Such heterocyclyl groups can have a single ring or multiple condensed rings wherein the condensed rings may not contain a heteroatom and/or may contain an aryl or a heteroaryl moiety, provided that the point of attachment is through an atom of the non-aromatic heterocyclyl group. Examples of heterocyclyl include pyrrolidinyl, piperadinyl, piperazinyl, and the like. Heterocyclyl rings are preferably saturated, though, heterocyclyl rings including 1-2 carbon carbon double bonds are also contemplated provided that the ring is not aromatic.

As used herein, "hydrogenation conditions" refer to conditions including hydrogen gas at atmospheric or higher pressure and catalysts that catalyze the reaction of the hydrogen with a hydrogen reactive group, such as a benzyl group or a carbon carbon double/triple bond. Catalysts useful for hydrogenation include palladium, platinum, and rhodium metals and their oxides or hydroxides, preferably supported on a material such as carbon or alumina.

As used herein, "protecting group" or "Pg" refers to well known functional groups which, when bound to a functional group, render the resulting protected functional group inert to the reaction to be conducted on other portions of the compound and the corresponding reaction condition, and which can be reacted to regenerate the original functionality under deprotection conditions. The protecting group is selected to be compatible with the remainder of the molecule. In one embodiment, the protecting group is an "amine protecting group" which protects an —NH— or an —NH$_2$— moiety, for example during the syntheses described here. Examples of amine protecting groups include, for instance, benzyl, acetyl, oxyacetyl, carbonyloxybenzyl (Cbz), Fmoc, and the like. In another embodiment, the protecting group is a "hydroxy protecting group" which protects a hydroxyl functionality during the synthesis described here. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, and benzyl. As the skilled artisan would appreciate, one or more of these protecting groups are also useful as amine protecting groups. Additional examples of amine, hydroxy, and keto protecting groups are found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting hydroxyl, —NH—, —NH$_2$—, and keto groups disclosed herein can be found in the art, and specifically in Greene and Wuts, supra, and the references cited therein.

As used herein, a "Lewis acid" refers to a compound that can donate a lone electron pair.

As used herein, a "non nucleophilic base" refers to a base that is capable of abstracting an acidic hydrogen, e.g., from an —OH or —NH— moiety, but does not readily take part in a nucleophilic substitution reaction. Preferably such bases are metal hydrides such as alkali metal hydrides or $CaH_2$.

As used herein, "oxidizing agent" refers to a compound that can accept electrons, and e.g., convert a CH(OH) group to a keto group. Examples of oxidizing agents are well known, and non limiting examples include hexavalent chromium reagents such as pyridinium chlorochromate, pyridinium dichromate, hypervalent iodine, and hypochlorite.

As used herein, "reducing agent" refers to a compounds that can donate electrons or a hydride in a reaction. Preferred examples include borohydrides such as $NaBH_4/CeCl_3$, and alanes such as diisobutyl aluminum hydride.

As used herein, a salt refers to preferably a salt of a mineral acid, or an organic acid such as a carboxylic acid or a sulfonic acid, and/or to alkali, alkaline earth, and various ammonium (including tetraalkyl ammonium, pyridinum, imidazolium and the like) salts. Non limiting examples of acid salts include salts of hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, and citric acid.

As used herein, the term "((S)-binol)" refers to the (S)-enantiomer of 1,1'-bi-2-naphthol, and "((R)-binol)" refers to the (R)-enantiomer of 1,1'-bi-2-naphthol.

As used herein, "silyl" refers to $Si(R^z)_3$ wherein each $R^z$ independently is $C_1$-$C_6$ alkyl or $C_6$-$C_{10}$ aryl.

As used herein, "substantially enantiomerically enriched," "substantially enantiomerically pure" or "substantial enantiomeric excess" or grammatical equivalents thereof refers to an enantiomer in an enantiomeric mixture with at least 95% ee, preferably 98% ee, or more preferably 99% ee.

Compounds of the Invention

In one aspect, this invention provides compounds of Formulas (I) and (VI):

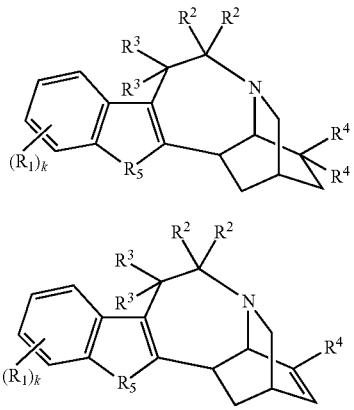

or a salt or enantiomer thereof wherein k is 1, 2, or 3;

each $R^1$ is independently selected from the group consisting of hydrogen, halo, amino, hydroxy, $C_1$-$C_6$ alkoxy, $C_1$-$C_6$ alkyl, $C_2$-$C_6$ alkenyl, $C_2$-$C_6$ alkynyl, cyano, nitro, —$N_3$, and —$CO_2H$ or an ester thereof, wherein the alkyl, alkoxy, alkenyl, or the alkylnyl group is optionally substituted with 1-3 substituents selected from the group consisting of keto, halo, amino, hydroxy, cyano, nitro, —$N_3$, phenyl optionally substituted with 1-3 substituents selected from the group consisting of $C_1$-$C_6$ alkyl and $C_1$-$C_6$ alkoxy, and —$CO_2H$ or an ester thereof;

$R^2$ is hydrogen or $C(R^2)_2$ is a keto group;

$R^3$ is selected from the group consisting of hydrogen, halo, $C_1$-$C_6$ alkyl, $C_2$-$C_6$ alkenyl, $C_2$-$C_6$ alkynyl, wherein the alkyl, alkenyl, or the alkylnyl group is optionally substituted with 1-3 substituents selected from the group consisting of keto, halo, amino, hydroxy, cyano, nitro, —$N_3$, and —$CO_2H$ or an ester thereof;

each $R^4$ independently is selected from the group consisting of hydrogen, hydroxy, —$SR^{41}$, —$OR^{42}$, $C_1$-$C_6$ alkyl, $C_2$-$C_6$ alkenyl, and $C_2$-$C_6$ alkynyl, wherein the alkyl, alkenyl, or the alkynyl group is optionally substituted with 1-3 substituents selected from the group consisting of keto, halo, $C_1$-$C_6$ alkoxy, amino, hydroxy, cyano, nitro, —$NHCOCH_3$, —$N_3$, and —$CO_2H$ or an ester thereof, or the 2 $R^4$ groups together with the carbon atom to which they are bonded to form a keto (C=O) group, a Schiff base (=$NR^{43}$), a vinylidene moiety of formula =$CR^{48}R^{49}$, or form a cyclic ketal or thioketal, which cyclic ketal or thioketal is of formula:

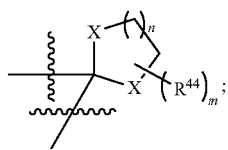

each $R^{41}$ is independently selected from the group consisting of $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof, $C_2$-$C_6$ alkenyl, $C_2$-$C_6$ alkynyl, $C_6$-$C_{10}$ aryl, $C_2$-$C_{10}$ heteroaryl, $C_3$-$C_8$ cycloalkyl, and $C_3$-$C_8$ heterocyclyl;

each $R^{42}$ is independently selected from the group consisting of $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof, $C_2$-$C_6$ alkenyl, and $C_2$-$C_6$ alkynyl;

where X in both occurrences is either oxygen or sulfur;

m is 1, 2, 3, or 4;

n is 1 or 2;

$R^{43}$ is selected from the group consisting of $C_6$-$C_{10}$ aryl and $C_2$-$C_{10}$ heteroaryl;

$R^{44}$ is selected from the group consisting of $C_1$-$C_6$ alkyl and $C_6$-$C_{10}$ aryl;

$R^{48}$ is hydrogen, $C_1$-$C_6$ alkyl, $C_2$-$C_6$ alkenyl, and $C_2$-$C_6$ alkynyl, wherein the alkyl, alkenyl, or the alkynyl group is optionally substituted with 1-3 substituents selected from the group consisting of keto, $C_1$-$C_6$ alkoxy, amino, hydroxy, cyano, nitro, —$NHCOCH_3$, and —$CO_2H$ or an ester thereof;

$R^{49}$ is hydrogen or $C_1$-$C_6$ alkyl;

$R^5$ is selected from the group consisting of —O— and N—$R^{51}$; and $R^{51}$ is selected from the group consisting of hydrogen and $C_1$-$C_6$ alkyl optionally substituted with 1-3 substituents selected from the group consisting of keto, halo, amino, hydroxy, cyano, nitro, —$N_3$, and —$CO_2H$ or an ester thereof;

wherein the $C^{14}$ content of a compound of Formula (I), that is tabernanthine, ibogamine, ibogaline, ibogamine, and noribogaine is less than 0.9 ppt, preferably less than 0.8 ppt, or more preferably less than 0.8 ppt.

A keto substituent, as used herein, substitutes a —$CH_2$— group to a —C(=O)-group. In one embodiment, the compound of Formula (I) excludes a compound selected from Iboga alkaloids. As used herein, Iboga alkaloids are alkaloids, isolated from the plant Tabernanthe Iboga that contain a tryptamine and an isoquinuclidene moiety as present in ibogaine or noribogaine. In one embodiment, the excluded iboga alkaloid is tabernanthine, ibogamine, ibogaline, ibogamine, or noribogaine.

In one embodiment, the compound of Formula (I) is of Formula (IA) or (IB):

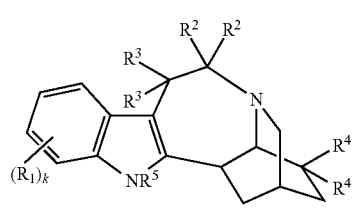

-continued (IB)
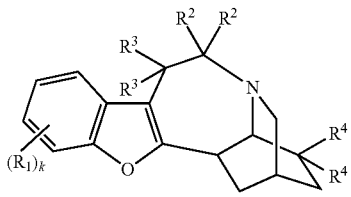

wherein k and $R^1$, $R^2$, $R^3$, $R^4$, and $R^5$ are defined as in Formula (I) above.

In another embodiment, the compound of Formula (I) is of Formula (IIA) or (IIB):

(IIA)
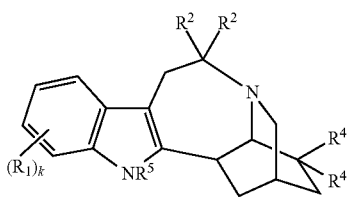

(IIB)
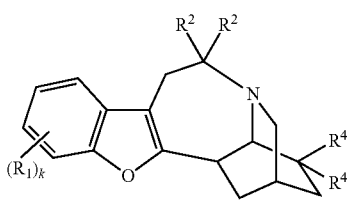

wherein k and $R^1$, $R^2$, $R^4$, and $R^5$ are defined as in Formula (I) above.

In another embodiment, the compound of Formula (I) is of Formula (IIIA) or (IIIB):

(IIIA)
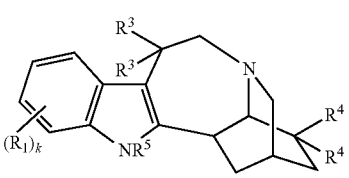

(IIIB)
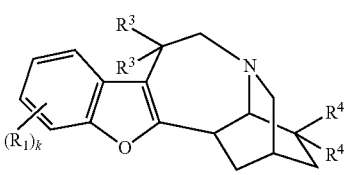

wherein k and $R^1$, $R^3$, $R^4$, and $R^5$ are defined as in Formula (I) above.

In another embodiment, the compound of Formula (I) is of Formula (IVA) or (IVB):

(IVA)
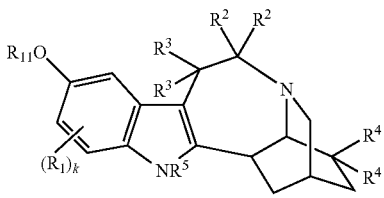

(IVB)
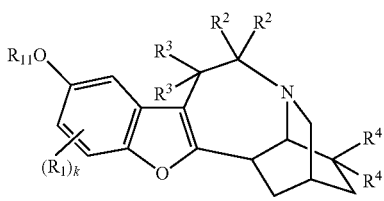

wherein $R^{11}$ is selected from the group consisting of hydrogen and $C_1$-$C_6$ alkyl optionally substituted with 1-3 substituents selected from the group consisting of halo, amino, hydroxy, cyano, nitro, —$N_3$, —$CO_2H$ or an ester thereof, and phenyl optionally substituted with 1-3 substituents selected from the group consisting of $C_1$-$C_6$ alkyl and $C_1$-$C_6$ alkoxy;
k is 1 or 2;
and $R^1$, $R^2$, $R^3$, $R^4$, and $R^5$ are defined as in Formula (I) above.

In another embodiment, the compound of Formula (I) is of Formula (IVC), (IVD), (VIA), or (VIB):

(IVC)
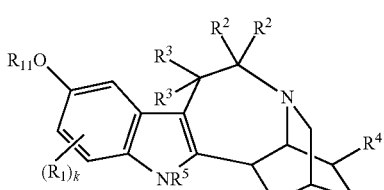

(IVD)
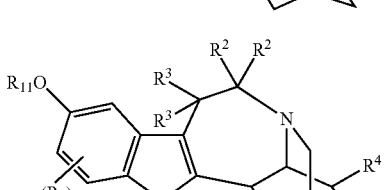

(VIA)
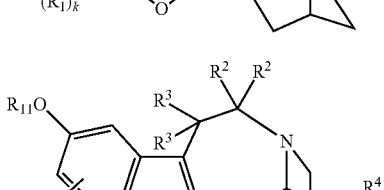

(VIB)
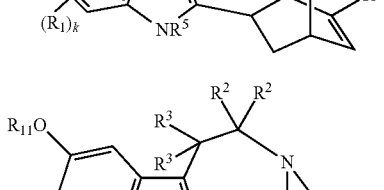

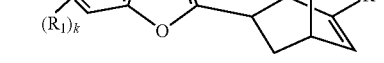

wherein $R^{11}$ is selected from the group consisting of hydrogen and $C_1$-$C_6$ alkyl optionally substituted with 1-3 substituents selected from the group consisting of halo, amino, hydroxy, cyano, nitro, —$N_3$, and —$CO_2H$ or an ester thereof, and phenyl optionally substituted with 1-3 substituents selected from the group consisting of $C_1$-$C_6$ alkyl and $C_1$-$C_6$ alkoxy;

k is 1 or 2;

and $R^1$, $R^2$, $R^3$, $R^4$, and $R^5$ are defined as in Formula (I) above.

In another embodiment, the present invention provides compounds of formula (VA):

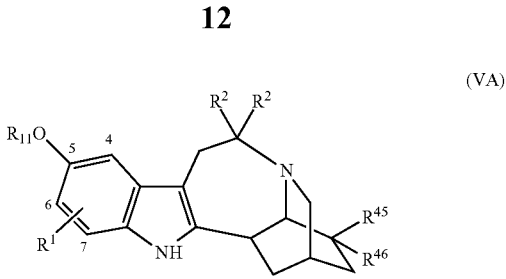
(VA)

as tabulated below:

| $R^1$ | $R^{11}$ | $C(R^2)_2$ | $R^{45}$ | $R^{46}$ | $R^{47}$ |
|---|---|---|---|---|---|
| H, 4-Me, 6-Me, 7-Me, 4-OH, 6-OH, 7-OH, 4-OMe, 6-OMe, or 7-OMe | Bn | C=O | $CR^{45}CR^{46}$ is C=O | — | — |
| H, 4-Me, 6-Me, 7-Me, 4-OH, 6-OH, 7-OH, 4-OMe, 6-OMe, or 7-OMe | Bn | C=O | $CR^{45}CR^{46}$ is C=$CR^{48}$H, $R^{48}$ is Me, Et, Pr, Bu | — | — |
| H, 4-Me, 6-Me, 7-Me, 4-OH, 6-OH, 7-OH, 4-OMe, 6-OMe, or 7-OMe | Bn | $CH_2$ | $CR^{45}CR^{46}$ is C=$CR^{48}$H, $R^{48}$ is Me, Et, Pr, Bu | — | — |
| H, 4-Me, 6-Me, 7-Me, 4-OH, 6-OH, 7-OH, 4-OMe, 6-OMe, or 7-OMe | Bn | C=O | CH=$CHR^{47}$ | OH | H or $C_1$-$C_4$ alkyl (e.g., Me, Et, Pr, Bu) optionally substituted with an OMe group (e.g., $CH_2$OMe, $(CH_2)_2$OMe, $(CH_2)_3$OMe, and $(CH_2)_4$OMe), OH group (e.g., $CH_2$OH, $(CH_2)_2$OH, $(CH_2)_3$OH, and $(CH_2)_4$OH), an amide (e.g., $(CH_2)_2$NHCOMe, $(CH_2)_3$NHCOMe, and $(CH_2)_4$NHCCOMe) or with an amino group (e.g., [azetidinyl], [pyrrolidinyl], [piperazinyl], or [morpholinyl]) |
| H, 4-Me, 6-Me, 7-Me, 4-OH, 6-OH, 7-OH, 4-OMe, 6-OMe, or 7-OMe | Bn | C=O | C=$CR^{47}$ | OH | H or $C_1$-$C_4$ alkyl (e.g., Me, Et, Pr, Bu) optionally substituted with an OMe group (e.g., $CH_2$OMe, $(CH_2)_2$OMe, $(CH_2)_3$OMe, and $(CH_2)_4$OMe), OH group (e.g., $CH_2$OH, $(CH_2)_2$OH, $(CH_2)_3$OH, and $(CH_2)_4$OH), an amide (e.g., $(CH_2)_2$NHCOMe, $(CH_2)_3$NHCOMe, and $(CH_2)_4$NHCCOMe) or with an amino group (e.g., [azetidinyl], [pyrrolidinyl], [piperazinyl], or [morpholinyl]) |

-continued

| R¹ | R¹¹ | C(R²)₂ | R⁴⁵ | R⁴⁶ | R⁴⁷ |
|---|---|---|---|---|---|
| H, 4-Me, 6-Me, 7-Me, 4-OH, 6-OH, 7-OH, 4-OMe, 6-OMe, or 7-OMe | Bn | C=O | CH₂CH₂R⁴⁷ | H | $C_1$-$C_4$ alkyl (e.g., Me, Et, Pr, Bu) optionally substituted with an OMe group (e.g., CH₂OMe, (CH₂)₂OMe, (CH₂)₃OMe, and (CH₂)₄OMe), OH group (e.g., CH₂OH, (CH₂)₂OH, (CH₂)₃OH, and (CH₂)₄OH), an amide (e.g., (CH₂)₂NHCOMe, (CH₂)₃NHCOMe, and (CH₂)₄NHCCOMe) or with an amino group (e.g., 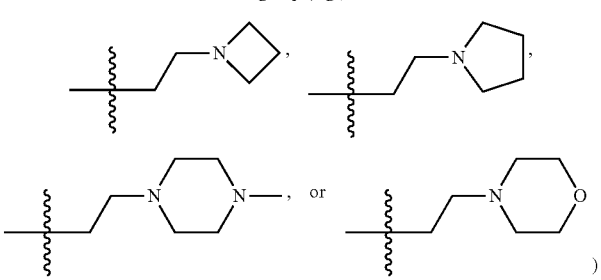) |
| H, 4-Me, 6-Me, 7-Me, 4-OH, 6-OH, 7-OH, 4-OMe, 6-OMe, or 7-OMe | Bn | C=O | CH₂CH₂R⁴⁷ | OH | $C_1$-$C_4$ alkyl (e.g., Me, Et, Pr, Bu) optionally substituted with an OMe group (e.g., CH₂OMe, (CH₂)₂OMe, (CH₂)₃OMe, and (CH₂)₄OMe), OH group (e.g., CH₂OH, (CH₂)₂OH, (CH₂)₃OH, and (CH₂)₄OH), an amide (e.g., (CH₂)₂NHCOMe, (CH₂)₃NHCOMe, and (CH₂)₄NHCCOMe) or with an amino group (e.g., 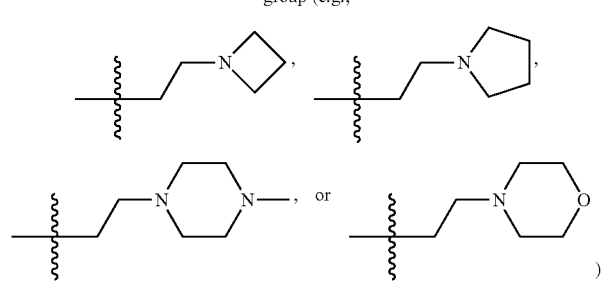) |
| H, 4-Me, 6-Me, 7-Me, 4-OH, 6-OH, 7-OH, 4-OMe, 6-OMe, or 7-OMe | Bn | CH₂ | CH=CHR⁴⁷ | OH | H or $C_1$-$C_4$ alkyl (e.g., Me Et, Pr, Bu) optionally substituted with an OMe group (e.g., CH₂OMe, (CH₂)₂OMe, (CH₂)₃OMe, and (CH₂)₄OMe), OH group (e.g., CH₂OH, (CH₂)₂OH, (CH₂)₃OH, and (CH₂)₄OH), an amide (e.g., (CH₂)₂NHCOMe, (CH₂)₃NHCOMe, and (CH₂)₄NHCCOMe) or with an amino group (e.g., 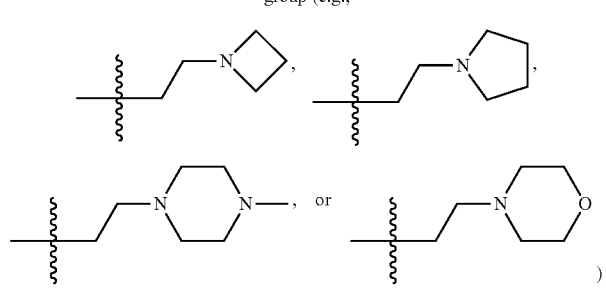) |

-continued

| $R^1$ | $R^{11}$ | $C(R^2)_2$ | $R^{45}$ | $R^{46}$ | $R^{47}$ |
|---|---|---|---|---|---|
| H, 4-Me, 6-Me, 7-Me, 4-OH, 6-OH, 7-OH, 4-OMe, 6-OMe, or 7-OMe | Bn | $CH_2$ | $C\equiv CR^{47}$ | OH | H or $C_1$-$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 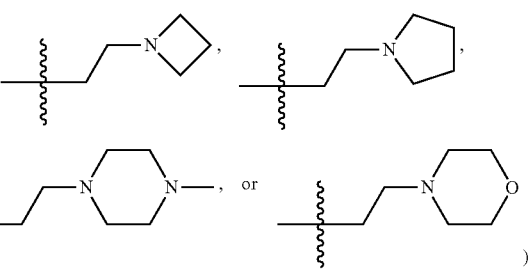) |
| H, 4-Me, 6-Me, 7-Me, 4-OH, 6-OH, 7-OH, 4-OMe, 6-OMe, or 7-OMe | Bn | $CH_2$ | $CH_2CH_2R^{47}$ | H | $C_1$-$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 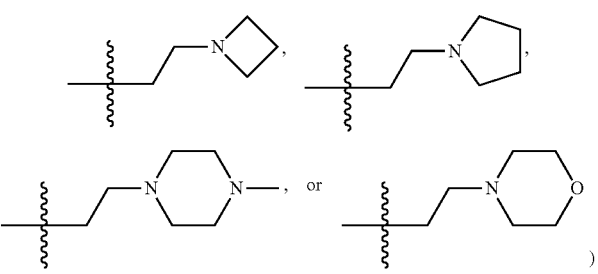) |
| H, 4-Me, 6-Me, 7-Me, 4-OH, 6-OH, 7-OH, 4-OMe, 6-OMe, or 7-OMe | Bn | $CH_2$ | $CH_2CH_2R^{47}$ | OH | $C_1$-$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 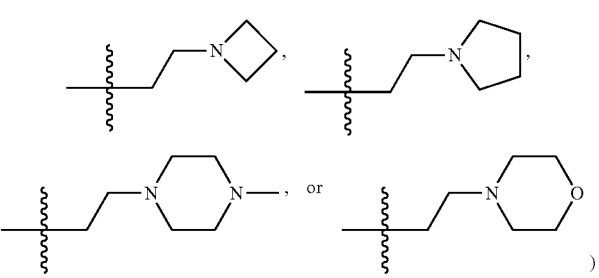) |

-continued

| $R^1$ | $R^{11}$ | $C(R^2)_2$ | $R^{45}$ | $R^{46}$ | $R^{47}$ |
|---|---|---|---|---|---|
| H, 4-Me, 6-Me, 7-Me, 4-OH, 6-OH, 7-OH, 4-OMe, 6-OMe, or 7-OMe | H | C=O | CH=CHR$^{47}$ | OH | H or C$_1$-C$_4$ alkyl (e.g., Me, Et, Pr, Bu) optionally substituted with an OMe group (e.g., CH$_2$OMe, (CH$_2$)$_2$OMe, (CH$_2$)$_3$OMe, and (CH$_2$)$_4$OMe), OH group (e.g., CH$_2$OH, (CH$_2$)$_2$OH, (CH$_2$)$_3$OH, and (CH$_2$)$_4$OH), an amide (e.g., (CH$_2$)$_2$NHCOMe, (CH$_2$)$_3$NHCOMe, and (CH$_2$)$_4$NHCCOMe) or with an amino group (e.g., CO$_2$(CH$_2$)$_2$NMe$_2$, 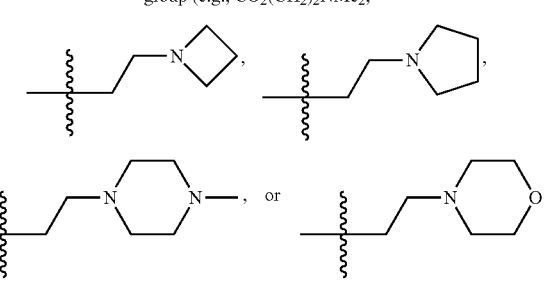) |
| H, 4-Me, 6-Me, 7-Me, 4-OH, 6-OH, 7-OH, 4-OMe, 6-OMe, or 7-OMe | H | C=O | C≡CR$^{47}$ | OH | H or C$_1$-C$_4$ alkyl (e.g., Me, Et, Pr, Bu) optionally substituted with an OMe group (e.g., CH$_2$OMe, (CH$_2$)$_2$OMe, (CH$_2$)$_3$OMe, and (CH$_2$)$_4$OMe), OH group (e.g., CH$_2$OH, (CH$_2$)$_2$OH, (CH$_2$)$_3$OH, and (CH$_2$)$_4$OH), an amide (e.g., (CH$_2$)$_2$NHCOMe, (CH$_2$)$_3$NHCOMe, and (CH$_2$)$_4$NHCCOMe) or with an amino group (e.g., CO$_2$(CH$_2$)$_2$NMe$_2$, 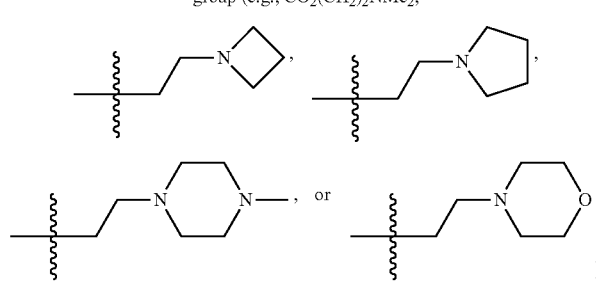) |
| H, 4-Me, 6-Me, 7-Me, 4-OH, 6-OH, 7-OH, 4-OMe, 6-OMe, or 7-OMe | H | C=O | CH$_2$CH$_2$R$^{47}$ | H | C$_1$-C$_4$ alkyl (e.g., Me, Et, Pr, Bu) optionally substituted with an OMe group (e.g., CH$_2$OMe, (CH$_2$)$_2$OMe, (CH$_2$)$_3$OMe, and (CH$_2$)$_4$OMe), OH group (e.g., CH$_2$OH, (CH$_2$)$_2$OH, (CH$_2$)$_3$OH, and (CH$_2$)$_4$OH), an amide (e.g., (CH$_2$)$_2$NHCOMe, (CH$_2$)$_3$NHCOMe, and (CH$_2$)$_4$NHCCOMe) or with an amino group (e.g., CO$_2$(CH$_2$)$_2$NMe$_2$, 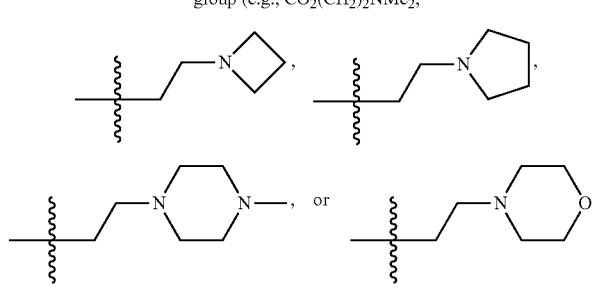) |

-continued

| $R^1$ | $R^{11}$ | $C(R^2)_2$ | $R^{45}$ | $R^{46}$ | $R^{47}$ |
|---|---|---|---|---|---|
| H, 4-Me, 6-Me, 7-Me, 4-OH, 6-OH, 7-OH, 4-OMe, 6-OMe, or 7-OMe | H | C=O | $CH_2CH_2R^{47}$ | OH | $C_1$-$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 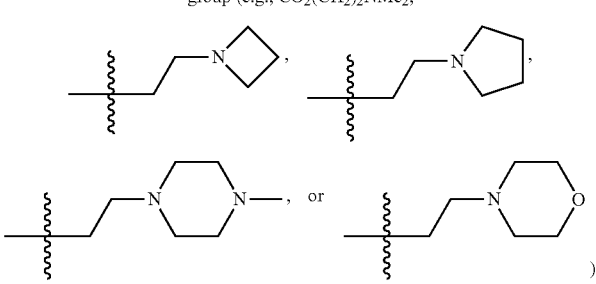) |
| H, 4-Me, 6-Me, 7-Me, 4-OH, 6-OH, 7-OH, 4-OMe, 6-OMe, or 7-OMe | H | $CH_2$ | $CH=CHR^{47}$ | OH | H or $C_1$-$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 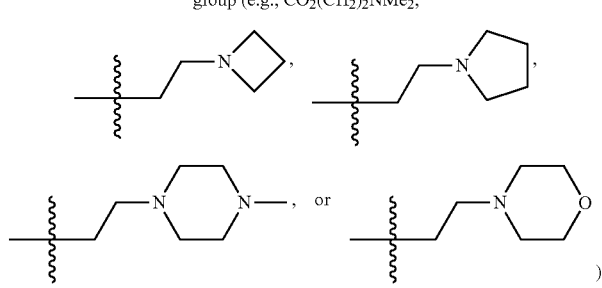) |
| H, 4-Me, 6-Me, 7-Me, 4-OH, 6-OH, 7-OH, 4-OMe, 6-OMe, or 7-OMe | H | $CH_2$ | $C≡CR^{47}$ | OH | H or $C_1$-$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 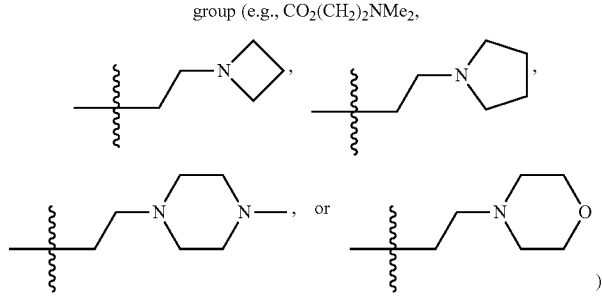) |

-continued

| R$^1$ | R$^{11}$ | C(R$^2$)$_2$ | R$^{45}$ | R$^{46}$ | R$^{47}$ |
|---|---|---|---|---|---|
| H, 4-Me, 6-Me, 7-Me, 4-OH, 6-OH, 7-OH, 4-OMe, 6-OMe, or 7-OMe | H | CH$_2$ | CH$_2$CH$_2$R$^{47}$ | H | C$_1$-C$_4$ alkyl (e.g., Me, Et, Pr, Bu) optionally substituted with an OMe group (e.g., CH$_2$OMe, (CH$_2$)$_2$OMe, (CH$_2$)$_3$OMe, and (CH$_2$)$_4$OMe), OH group (e.g., CH$_2$OH, (CH$_2$)$_2$OH, (CH$_2$)$_3$OH, and (CH$_2$)$_4$OH), an amide (e.g., (CH$_2$)$_2$NHCOMe, (CH$_2$)$_3$NHCOMe, and (CH$_2$)$_4$NHCCOMe) or with an amino group (e.g., CO$_2$(CH$_2$)$_2$NMe$_2$, 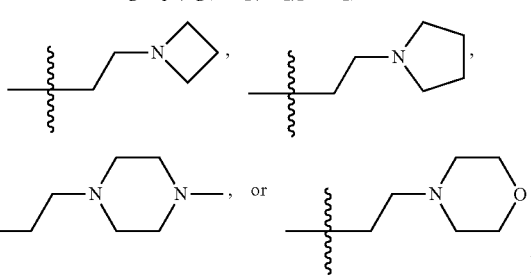) |
| H, 4-Me, 6-Me, 7-Me, 4-OH, 6-OH, 7-OH, 4-OMe, 6-OMe, or 7-OMe | H | CH$_2$ | CH$_2$CH$_2$R$^{47}$ | OH | C$_1$-C$_4$ alkyl (e.g., Me, Et, Pr, Bu) optionally substituted with an OMe group (e.g., CH$_2$OMe, (CH$_2$)$_2$OMe, (CH$_2$)$_3$OMe, and (CH$_2$)$_4$OMe), OH group (e.g., CH$_2$OH, (CH$_2$)$_2$OH, (CH$_2$)$_3$OH, and (CH$_2$)$_4$OH), an amide (e.g., (CH$_2$)$_2$NHCOMe, (CH$_2$)$_3$NHCOMe, and (CH$_2$)$_4$NHCCOMe) or with an amino group (e.g., CO$_2$(CH$_2$)$_2$NMe$_2$, 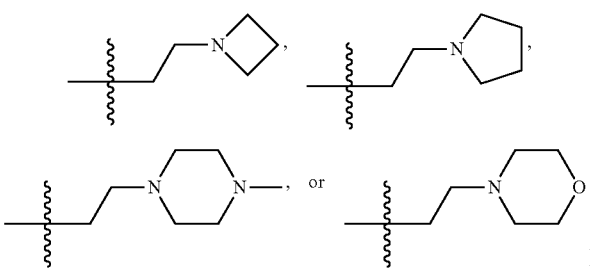) |

In another embodiment, this invention provides a compound of Formula (VIC):

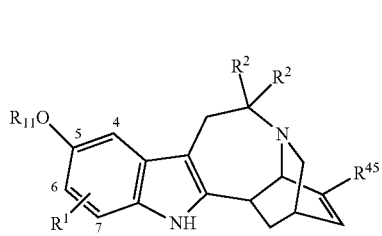

(VIC)

as tabulated below:

| $R^1$ | $R^{11}$ | $C(R^2)_2$ | $R^{45}$ | $R^{47}$ |
|---|---|---|---|---|
| H, 4-Me, 6-Me, 7-Me, 4-OH, 6-OH, 7-OH, 4-OMe, 6-OMe, or 7-OMe | Bn | C=O | CH=CHR$^{47}$ | H or $C_1$-$C_4$ alkyl (e.g., Me, Et, Pr, Bu) optionally substituted with an OMe group (e.g., $CH_2$OMe, $(CH_2)_2$OMe, $(CH_2)_3$OMe, and $(CH_2)_4$OMe), OH group (e.g., $CH_2$OH, $(CH_2)_2$OH, $(CH_2)_3$OH, and $(CH_2)_4$OH), an amide (e.g., $(CH_2)_2$NHCOMe, $(CH_2)_3$NHCOMe, and $(CH_2)_4$NHCCOMe) or with an amino group (e.g., $CO_2(CH_2)_2NMe_2$, 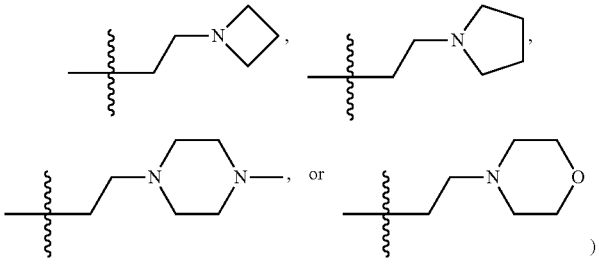) |
| H, 4-Me, 6-Me, 7-Me, 4-OH, 6-OH, 7-OH, 4-OMe, 6-OMe, or 7-OMe | Bn | C=O | C≡CR$^{47}$ | H or $C_1$-$C_4$ alkyl (e.g., Me, Et, Pr, Bu) optionally substituted with an OMe group (e.g., $CH_2$OMe, $(CH_2)_2$OMe, $(CH_2)_3$OMe, and $(CH_2)_4$OMe), OH group (e.g., $CH_2$OH, $(CH_2)_2$OH, $(CH_2)_3$OH, and $(CH_2)_4$OH), an amide (e.g., $(CH_2)_2$NHCOMe, $(CH_2)_3$NHCOMe, and $(CH_2)_4$NHCCOMe) or with an amino group (e.g., $CO_2(CH_2)_2NMe_2$, 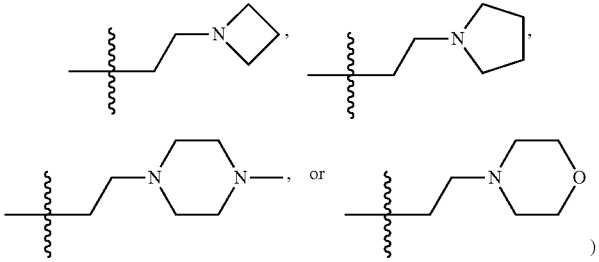) |
| H, 4-Me, 6-Me, 7-Me, 4-OH, 6-OH, 7-OH, 4-OMe, 6-OMe, or 7-OMe | Bn | C=O | $CH_2CH_2R^{47}$ | $C_1$-$C_4$ alkyl (e.g., Me, Et, Pr, Bu) optionally substituted with an OMe group (e.g., $CH_2$OMe, $(CH_2)_2$OMe, $(CH_2)_3$OMe, and $(CH_2)_4$OMe), OH group (e.g., $CH_2$OH, $(CH_2)_2$OH, $(CH_2)_3$OH, and $(CH_2)_4$OH), an amide (e.g., $(CH_2)_2$NHCOMe, $(CH_2)_3$NHCOMe, and $(CH_2)_4$NHCCOMe) or with an amino group (e.g., $CO_2(CH_2)_2NMe_2$, 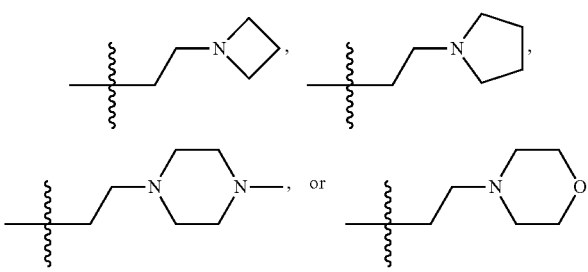) |

-continued

| $R^1$ | $R^{11}$ | $C(R^2)_2$ | $R^{45}$ | $R^{47}$ |
|---|---|---|---|---|
| H, 4-Me, 6-Me, 7-Me, 4-OH, 6-OH, 7-OH, 4-OMe, 6-OMe, or 7-OMe | Bn | $CH_2$ | $CH=CHR^{47}$ | H or $C_1$-$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 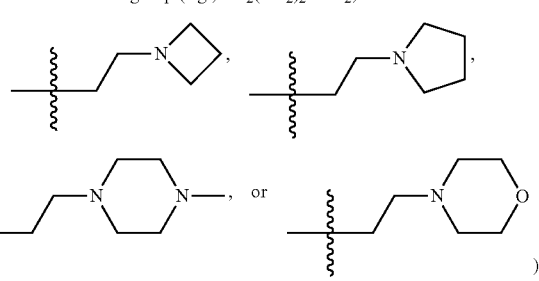) |
| H, 4-Me, 6-Me, 7-Me, 4-OH, 6-OH, 7-OH, 4-OMe, 6-OMe, or 7-OMe | Bn | $CH_2$ | $C\equiv CR^{47}$ | H or $C_1$-$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 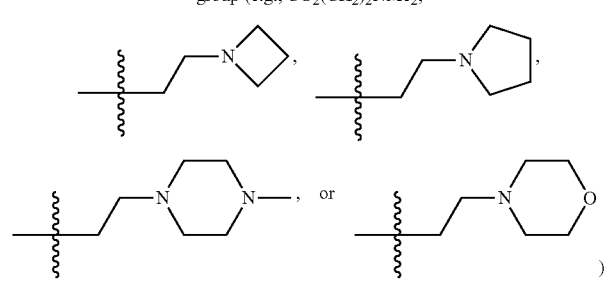) |
| H, 4-Me, 6-Me, 7-Me, 4-OH, 6-OH, 7-OH, 4-OMe, 6-OMe, or 7-OMe | Bn | $CH_2$ | $CH_2CH_2R^{47}$ | $C_1$-$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 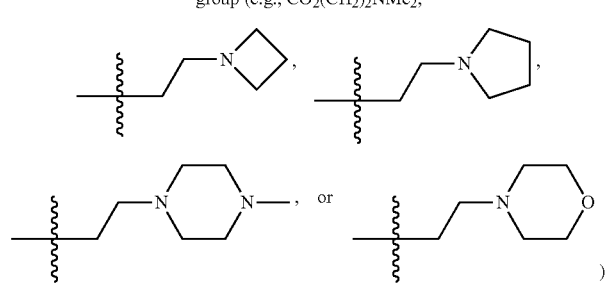) |

As used herein, Me, Et, Pr, Bu and Bn, refer to methyl, ethyl, propyl, butyl, and benzyl, respectively.

In another embodiment, this invention provides an isolated enantiomer of a compound of any one of Formulas (I), (IA), (IB), (IIA), (IIB), (IIIA), (IIIB), (IVA), (IVB), (IVC), (IVD), (VA), (VI), (VIA), (VIB), or (VIC) in substantial enantiomeric excess.

In one embodiment, this invention provides a compound of formula:

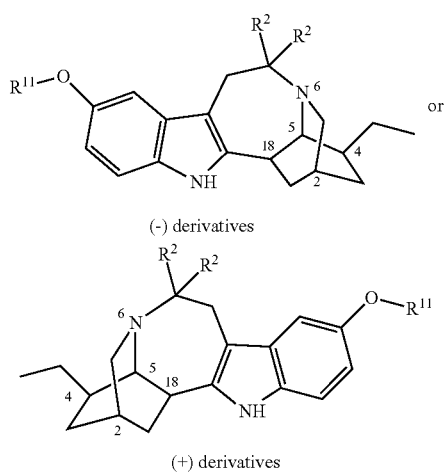

(−) derivatives (+) derivatives in a substantially enantiomeric ally enriched form, or a salt of each thereof, wherein $R^1$ is $C_1$-$C_4$ alkyl optionally substituted with a phenyl or a substituted phenyl group, wherein the substituted phenyl is substituted with 1-3 $C_1$-$C_4$ alkyl or $C_1$-$C_4$ alkoxy groups and $R_2$ is hydrogen or $C(R^2)_2$ is C=O.

In another embodiment, $R_2$ is hydrogen. In another embodiment, $C(R^2)_2$ is C=O. In another embodiment, $R^1$ is methyl or benzyl. In another embodiment, the compound is provided as an isolated enantiomer in substantial enantiomeric excess.

In another embodiment, this invention provides (+) noribogaine. In another embodiment, the (+) noribogaine has a $^{14}C$ content of less than 1 ppt, preferably less than 0.9 ppt, and more preferably less than 0.8 ppt.

$^{14}C$ has a half-life of about 5,730 years and is generated in the upper atmosphere as $^{14}CO_2$. The amount of $^{14}CO_2$ present is approximately 1 ppt (parts per trillion) and, through photosynthesis, accumulates in plants resulting in a $^{14}C$ content of plant material of approximately 1 ppt. Accordingly, plant derived compounds are expected to have approximately 1 ppt $^{14}C$. Conversely, the synthetic compounds disclosed herein are derived from fossil fuels, which, due to $^{14}C$ decay, would have a $^{14}C$ content of less than 1 ppt $^{14}C$. Accordingly, provided herein are synthetic indole and benzofuran fused isoquinuclidene derivative having a $^{14}C$ content of less than 1 ppt, preferably, less than 0.90 ppt, or more preferably less than 0.8 ppt.

Processes of the Invention

Compounds of this invention are prepared as schematically illustrated below:

Scheme 1

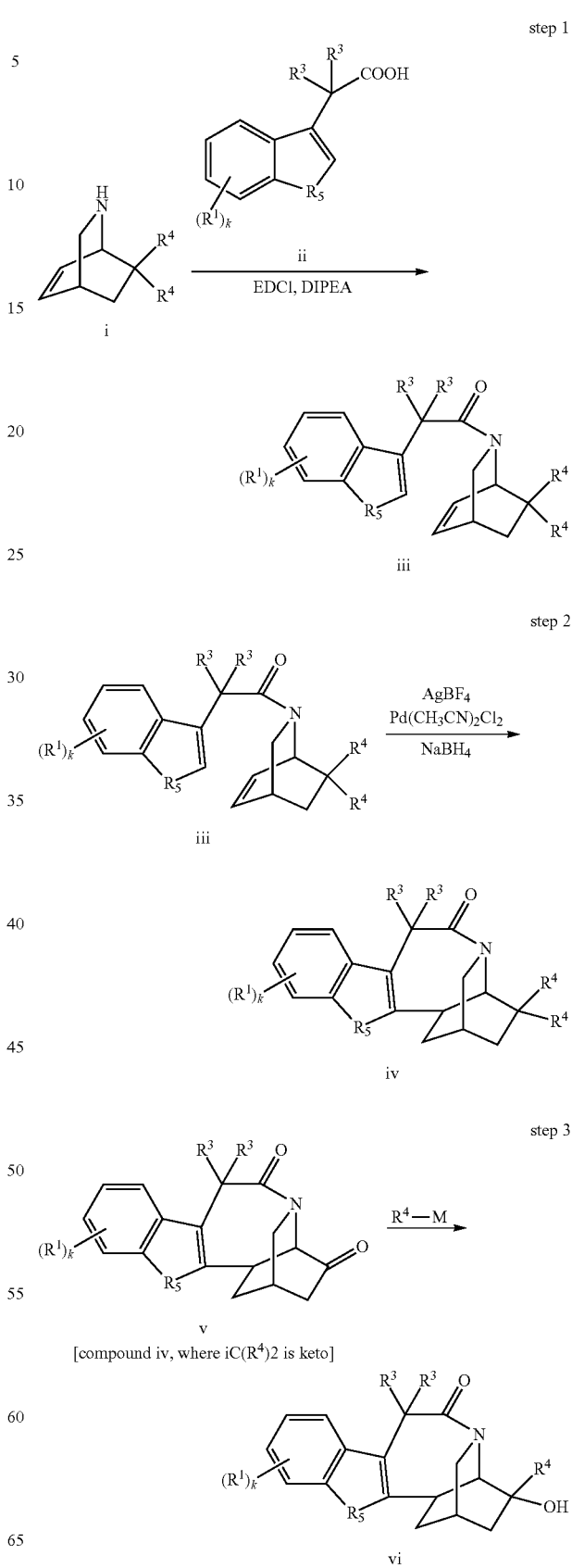

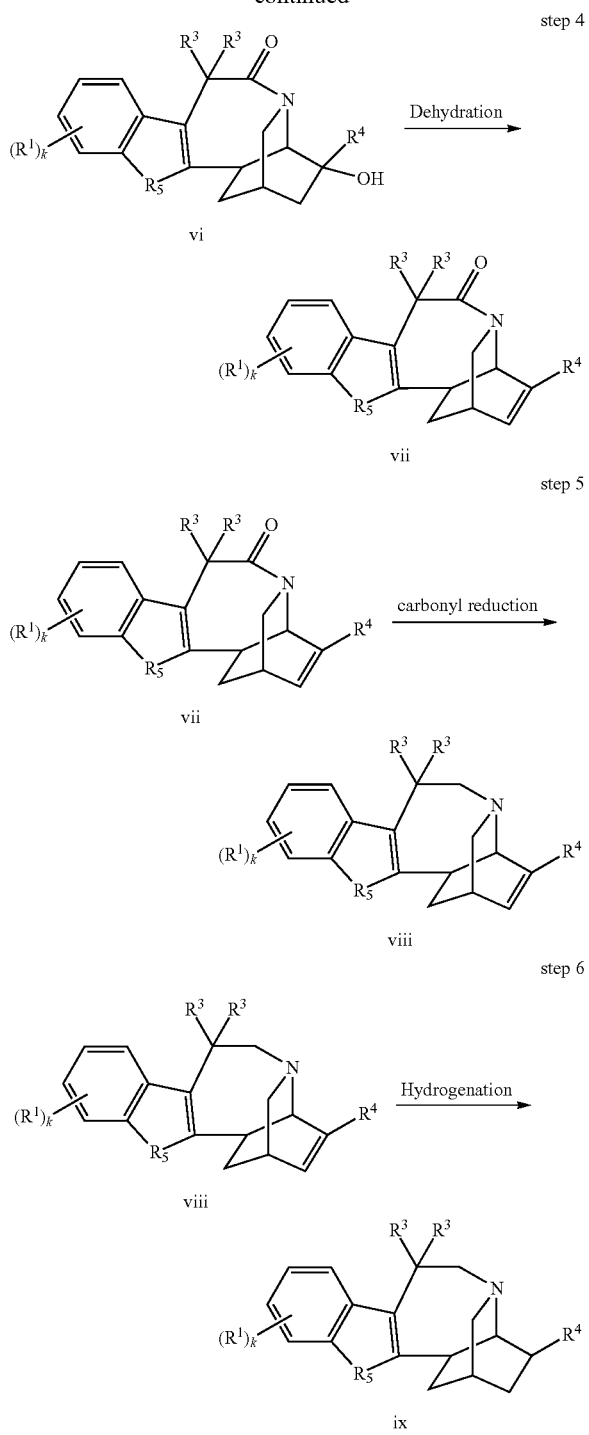

In the scheme above, k, $R^1$, $R^2$, $R^3$, and $R^5$ are defined as in any aspect or embodiment herein. Compound i is obtained, following the procedure described in U.S. application Ser. No. 13/358,446, which is incorporated herein in its entirety by reference. Compound ii is available commercially or prepared easily from commercially available material following steps well known in the art.

In one embodiment, this invention provides a process for preparing compound iii comprising contacting compound i with compound ii under conditions to provide compound iii. Accordingly, in step 1, compound i is coupled with compound ii, preferably in an inert solvent, in the presence of an amide or an ester coupling reagent. Various such coupling agents such as carbodiimides or (O-Benzotriazole-N,N,N', N'-tetramethyl uronium hexafluorophosphate) HBTU or (2-(1H-7-Azabenzotriazol-1-yl)-1,1,3,3-tetramethyl uronium hexafluorophosphate) HATU, and their immobilized derivatives are well known in the art and available commercially, for example, from Sigma-Aldrich Co. The reaction is carried out under suitable conditions to effect reaction completion. Typically, the reaction is carried out at 0-50° C. for a period of time sufficient to provide a substantial amount of the product, which can be ascertained by using routine methods such as thin layer chromatography, $^1$H-nuclear magnetic resonance (NMR) spectroscopy, and the likes. The product can be isolated and optionally purified using standard purification techniques, such as liquid chromatography, crystallization, and precipitation, or the products may be used for a subsequent reaction without further purification.

In another embodiment, this invention provides a process for preparing compound iv comprising subjecting compound iii under conditions to provide compound iv. Accordingly, in step 2, compound iii is made to undergo an intramolecular Heck type cyclization, preferably in an inert solvent, in the presence of 100-130 mole %, with respect to compound iii, of a Pd(II) salt, and an oxidant such as a silver (I). A reducing agent, such as a borohydride is used to reductively workup the reaction mixture to provide compound iv. The reaction is carried out at 30-90° C. for a period of time sufficient to provide a substantial amount of the product, which can be ascertained by using routine methods such as thin layer chromatography, NMR spectroscopy, and the likes. The product can be isolated and optionally purified using standard purification techniques, such as liquid chromatography, crystallization, and precipitation, or the products may be used for a subsequent reaction without further purification.

In another embodiment, this invention provides a process for preparing compound vi comprising contacting compound v with $R^4$-M, wherein $R^4$ is $C_1$-$C_6$ alkyl, $C_2$-$C_6$ alkenyl, or $C_3$-$C_6$ alkynyl, optionally substituted with a protected form of amino or hydroxy, and M is lithium or magnesium halide, under conditions to provide compound vi. Accordingly, in step 3, compound v, which is compound iv wherein $C(R^4)_2$ is a keto group, and which is readily obtained from compound iv, where $C(R^4)_2$ is a cyclic ketal or thioketal by deprotection, is reacted with an $R^4$ anion equivalent, $R^4$-M, wherein M is lithium, a magnesium halide, and the like. The reaction is carried out, preferably with about a 10 fold excess of the $R^4$-M in an inert solvent such as ether or tetrahydrofuran at a temperature of −5° C. to 15° C. for a period of time sufficient to provide a substantial amount of the product, which can be ascertained by using routine methods such as thin layer chromatography, $^1$H-nuclear magnetic resonance (NMR) spectroscopy, and the likes. After aqueous work-up using, for example, water, aqueous $NH_4Cl$ or aqueous tartrate, the product can be isolated and optionally purified using standard purification techniques, such as liquid chromatography, crystallization, and precipitation, or the products may be used for a subsequent reaction without further purification.

In another embodiment, this invention provides a process for preparing compound vii comprising subjecting compound vi under conditions to provide compound vii. Accordingly, in step 4, compound vi is dehydrated, preferably using an acid such as a sulfonic acid to provide compound vii. The dehydration is carried out in an inert solvent, preferably at a temperature where the solvent refluxes, for a period of time sufficient to provide a substantial amount of the product, which can be ascertained by using routine methods such as thin layer chromatography, NMR spectroscopy, and the likes. Various solvents useful for this purpose is well known in the art and will be apparent to the skilled artisan upon reading this disclosure. The product can be isolated and optionally purified using standard purification techniques, such as liquid chromatography, crystallization, and precipitation, or the products may be used for a subsequent reaction without further purification.

In another embodiment, this invention provides a process for preparing compound viii comprising subjecting compound vii under conditions to provide compound viii. Accordingly, in step 5, the amide carbonyl of compound vii is reduced to a —CH$_2$— moiety by reacting with a borohydride, optionally activated with a Lewis acid, such as BF$_3$ etherate, or with an aluminum hydride. The reaction is performed in an inert solvent, preferably, an ether or tetrahydrofuran at a temperature of 0-50° C. or in a refluxing solvent. The reaction is carried out for a period of time sufficient to provide a substantial amount of the product, which can be ascertained by using routine methods such as thin layer chromatography, NMR spectroscopy, and the likes. The product can be isolated and optionally purified using standard purification techniques, such as liquid chromatography, crystallization, and precipitation, or the products may be used for a subsequent reaction without further purification.

In another embodiment, this invention provides a process for preparing compound ix comprising subjecting compound viii under conditions to provide compound ix. Accordingly, in step 6, compound viii is hydrogenated to provide compound viii. The hydrogenation is carried out using Pd or Pt or their oxides or hydroxides adsorbed on a solid support such as carbon, alumina, and the like, preferably in an amount less than 100 mole % with respect to compound viii, and hydrogen. The hydrogenation is carried out in an inert solvent, such as an alcohol, ethyl acetate, or an ether, at 15-30° C. for a period of time sufficient to provide a substantial amount of the product, which can be ascertained by using routine methods such as thin layer chromatography, NMR spectroscopy, and the likes. The product can be isolated and optionally purified using standard purification techniques, such as liquid chromatography, crystallization, and precipitation.

In certain process embodiments, C(R$^4$)$_2$ is a keto (C=O) group. In other process embodiments, for compounds i and iii, C(R$^4$)$_2$ is cyclic ketal or thioketal. In other process embodiments, R$^5$ is NH. In certain other process embodiments, R$^5$ is O. In certain other process embodiments, for compounds, vi-ix, R$^4$ is C$_1$-C$_6$ alkyl, C$_2$-C$_6$ alkenyl, or C$_2$-C$_6$ alkynyl, optionally substituted with 1-3 substituents, as provided herein, or their protected forms that will be apparent to the skilled artisan.

It will be apparent to the skilled artisan upon reading this disclosure that the sequence of steps shown in Scheme 1, are preferred illustrative sequences, and can be altered in manners apparent to the skilled artisan to obtain the compounds provided herein.

Compounds of this invention where C(R$^4$)$_2$ is C=CR$^{48}$R$^{49}$ are conveniently prepared from the corresponding keto compound (C(R$^4$)$_2$ is keto) following Wittig and other related olefination procedures, as is well known to the skilled artisan.

In certain other of its process embodiments, this invention provides processes, preferably, enantioselective processes, for preparing (−) noribogaine, in a substantially enantiomerically pure form, as schematically illustrated below, where the reagents indicated are merely illustrative and are not limiting, as discussed in further detail below.

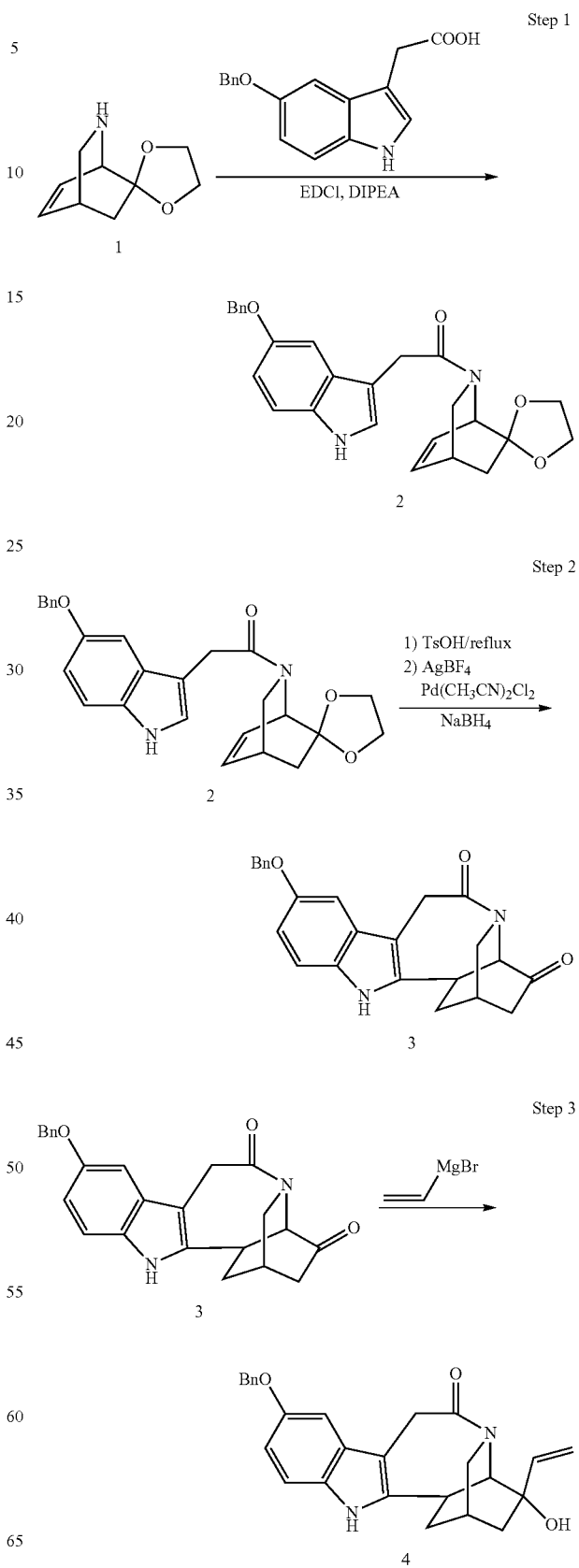

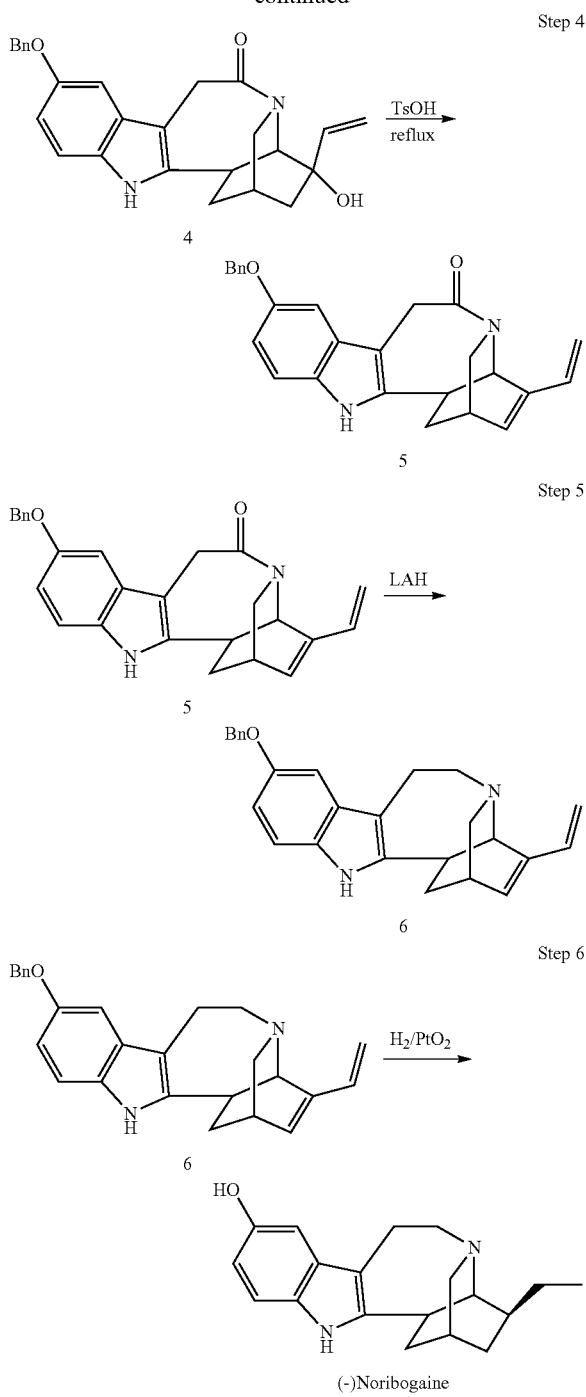

In one embodiment, this invention provides a process for preparing compound 2 comprising contacting compound 1 with 5-benzyloxyindoleacetic acid under conditions to provide compound 2. Thus, in step 1, Compound 1 is coupled with the benzyloxy substituted indole acetic acid to provide compound 2. The coupling is performed preferably in an inert solvent, such as a chlorinated solvent such as dichloromethane, or in tetrahydrofuran, or acetonitrile, in the presence of a amide or ester coupling reagent. Various such coupling agents such as carbodiimides or HBTU or HATU, and their immobilized derivatives are well known in the art and available commercially, for example, from Sigma-Aldrich Co. In a preferred embodiment, the coupling is performed in the presence of 1-ethyl-3-(3-dimethylaminopropyl)carbodiimide (EDCI) and a hindered base, such as diisopropylethyl amine (DIPEA). In one embodiment, The reaction is carried out at 0-50° C. for a period of time sufficient to provide a substantial amount of the product, which can be ascertained by using routine methods such as thin layer chromatography, NMR spectroscopy, and the likes. FIG. 3 demonstrates the $^1$H-NMR spectrum of compound 2. The product can be isolated and optionally purified using standard purification techniques, such as liquid chromatography, crystallization, and precipitation, or the product may be used for a subsequent reaction without further purification.

Figure 1:
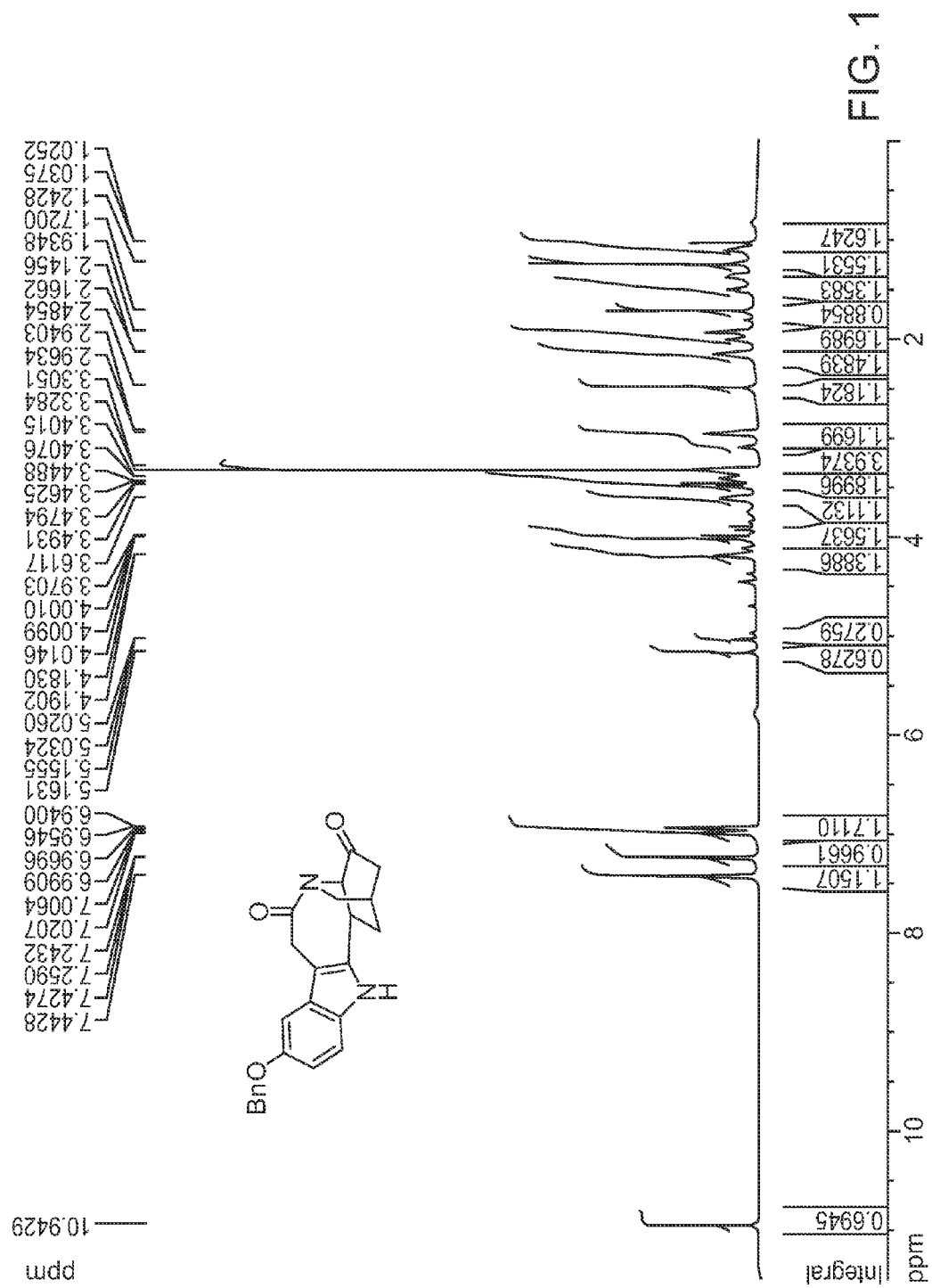
FIG. 1 illustrates a $^1$H-NMR spectrum in CDCl$_3$ of compound 3.

In another embodiment, this invention provides a process for preparing compound 3 comprising subjecting compound 2 under conditions to provide compound 3. Thus, in step 2, compound 2 is deprotected by reacting with an aqueous acid. Various mineral acids such as sulfuric acid or hydrochloric acid, and sulfonic acids, such as toluene sulfonic acid are useful as the acid. Following the deprotection, the deprotected compound is subjected to an intramolecular Heck type cyclization. Various art known palladium reagents, such as palladium chloride and complexes thereof (such as the bis acetonitrile complex) are useful as the cyclization reagent, used in 100-130 mole % with respect to compound 2, further in presence of an oxidant, such as a Ag(I) salt. Reductive workup, employing a borohydride was demonstrated to provide compound 3 (see, FIG. 1). The reaction is carried out in an inert solvent, such as acetonitrile, alcohols, acetic acid, and mixtures thereof, at 30-90° C., preferably at 60-80° C. for a period of time sufficient to provide a substantial amount of the product, which can be ascertained by using routine methods such as thin layer chromatography, NMR spectroscopy, and the likes. The product can be isolated and optionally purified using standard purification techniques, such as liquid chromatography, crystallization, and precipitation, or the product may be used for a subsequent reaction without further purification.

In another embodiment, this invention provides a process for preparing compound 4 comprising contacting compound 3 with an ethyl anion equivalent under conditions to provide compound 4. As used herein, an ethyl anion equivalent is an anion that after this reaction is easily converted to an ethyl group. Thus, in step 3, compound 3 is reacted with an ethyl anion equivalent, such as, vinyl magnesium bromide (in a 10 fold mole/mole excess with respect to compound 3), in ether, tetrahydrofuran or a mixture thereof to provide after aqueous work up, compound 4. The reaction is carried out for a period of time sufficient to provide a substantial amount of the product, which can be ascertained by using routine methods such as thin layer chromatography, NMR spectroscopy, and the likes. The product can be isolated and optionally purified using standard purification techniques, such as liquid chromatography, crystallization, and precipitation, or the product may be used for a subsequent reaction without further purification.

In another embodiment, this invention provides a process for preparing compound 5 comprising subjecting compound 4 under conditions to provide compound 5. Thus, in step 4, compound 4 is dehydrated to provide compound 5. The dehydration is performed preferably using an acid such as a sulfonic acid such as toluene sulfonic acid to provide compound vii. The dehydration is carried out in an inert solvent, preferably at a temperature where the solvent refluxes, for a period of time sufficient to provide a substantial amount of the product, which can be ascertained by using routine methods such as thin layer chromatography, NMR spectroscopy, and the likes. Various solvents useful for this purpose is well known in the art and will be apparent to the skilled artisan upon reading this disclosure. The product can be isolated and optionally purified using standard purification techniques, such as liquid chromatography, crystallization, and precipitation, or the product may be used for a subsequent reaction without further purification.

In another embodiment, this invention provides a process for preparing compound 6 comprising subjecting compound 5 under conditions to provide compound 6. Thus, in step 5, the amide carbonyl of compound 5 is reduced to provide compound 6, by reacting with a borohydride, optionally activated with a Lewis acid, such as $BF_3$ etherate, or with an aluminum hydride. A preferred reagent is lithium aluminum hydride. The reaction is performed in an inert solvent, preferably, an ether or tetrahydrofuran at a temperature of 0-50° C. or in a refluxing solvent. The reaction is carried out for a period of time sufficient to provide a substantial amount of the product, which can be ascertained by using routine methods such as thin layer chromatography, NMR spectroscopy, and the likes. The product can be isolated and optionally purified using standard purification techniques, such as liquid chromatography, crystallization, and precipitation, or the product may be used for a subsequent reaction without further purification.

In another embodiment, this invention provides a process for preparing (−) noribogaine or a salt thereof comprising subjecting compound 6 under conditions to provide (−) noribogaine or a salt thereof. In step 6, compound 6 is hydrogenated to provide (−) noribogaine or a salt thereof. The hydrogenation is carried out using Pd, Pt, Rh or their oxides or hydroxides adsorbed on a solid support such as carbon, alumina, and the like, preferably in an amount less than 100 mole % with respect to compound 6, and hydrogen. A preferred reagent is $PtO_2$. The hydrogenation is carried out in an inert solvent, such as an alcohol, ethyl acetate, or an ether. The hydrogenation is carried out at 15-30° C. for a period of time sufficient to provide a substantial amount of the product, which can be ascertained by using routine methods such as thin layer chromatography, NMR spectroscopy, and the likes.

The product can be isolated and optionally purified using standard purification techniques, such as liquid chromatography, crystallization, and precipitation. The compound obtained from compound 6 following the process described above showed the following $^1$H-NMR chemical shifts (7.27 (d), 7.05 (d), 6.8 (d), 3.85-3.72 (m), 3.67-3.58 (m), 3.54 (m), 3.44 (m), 3.32 (t), 2.42-2.28 (m), 2.27-2.14 (m), 2.00-1.77 (m), 1.63-1.54 (m), 1.23 (t)), which are the same as those observed for (−) noribogaine, thereby demonstrating the preparation of (−) noribogaine according to this invention.

It will be apparent to the skilled artisan upon reading this disclosure that certain sequence of steps shown in Scheme 2, are preferred illustrative sequences, and can be altered in manners apparent to the skilled artisan to obtain the compounds provided herein.

Compound 1, utilized in the processes above is prepared as illustrated schematically below:

Scheme 3

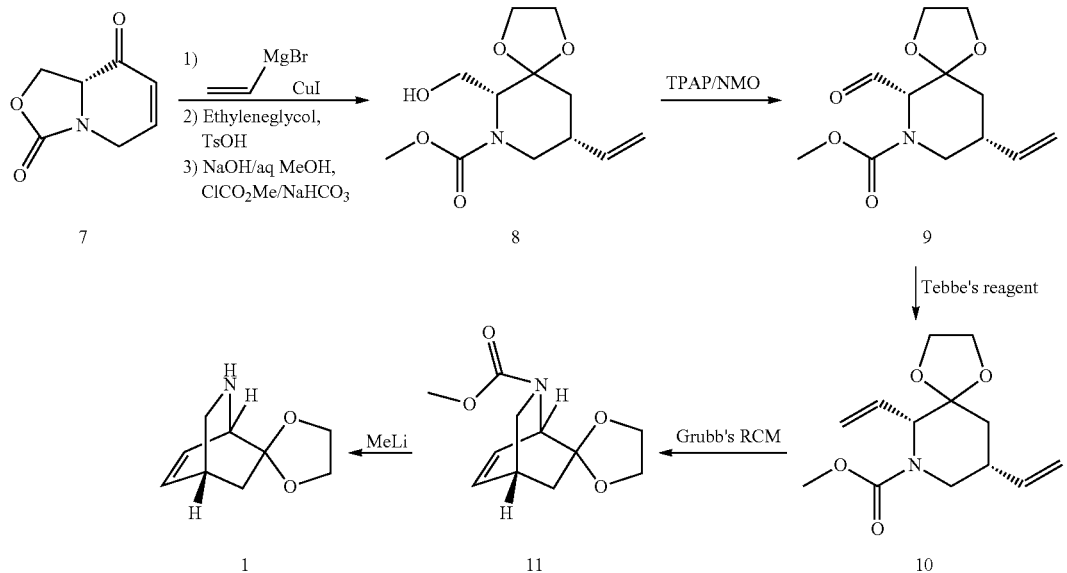

Conjugate addition of vinyl magnesium bromide, oxazolidine ring cleavage, and keto group protection converts compound 7 to compound 8. Compound 8 is oxidized using NMO and tetrapropylammonium perruthenate to provides compound 9. Olefination of 9 yields the 1,5 divinyl substrate piperidine (10). Grubbs ring closing metathesis cyclization of 10 using the well known and commercially available Grubbs' or Schrock catalysts yields optically active (11) which is the carbonyl group and N-protected derivative compound 6. Deprotection of compound 11 with methyl lithium was demonstrated to provide compound 1. The $^1$H-NMR of compound 1 is provided in FIG. 2. The reactions are carried out, preferably in an inert solvent that will be apparent to the skilled artisan upon reading this disclosure, and at temperatures that will also be apparent to the skilled artisan upon reading this disclosure. The reactions are performed for a period of time sufficient to provide a substantial amount of the product, which can be ascertained by using routine methods such as thin layer chromatography, $^1$H-nuclear magnetic resonance (NMR) spectroscopy, and the likes. The products can be isolated and optionally purified using standard purification techniques, such as liquid chromatography, crystallization, precipitation, and distillation under reduced pressure, or the products may be used for a subsequent reaction without further purification.
Other processes of this invention for preparing (−) and (+) noribogaine are schematically illustrated and described below.
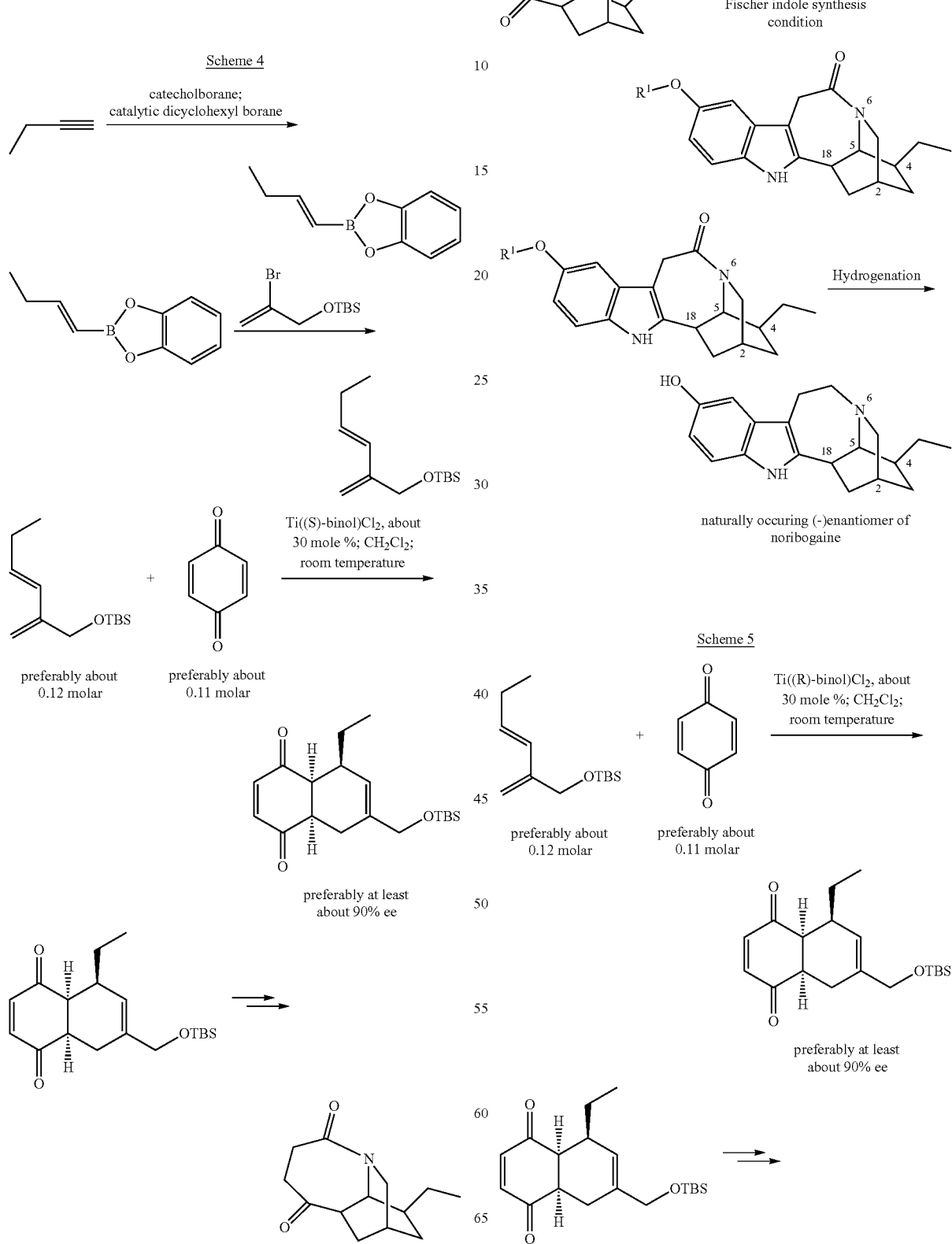

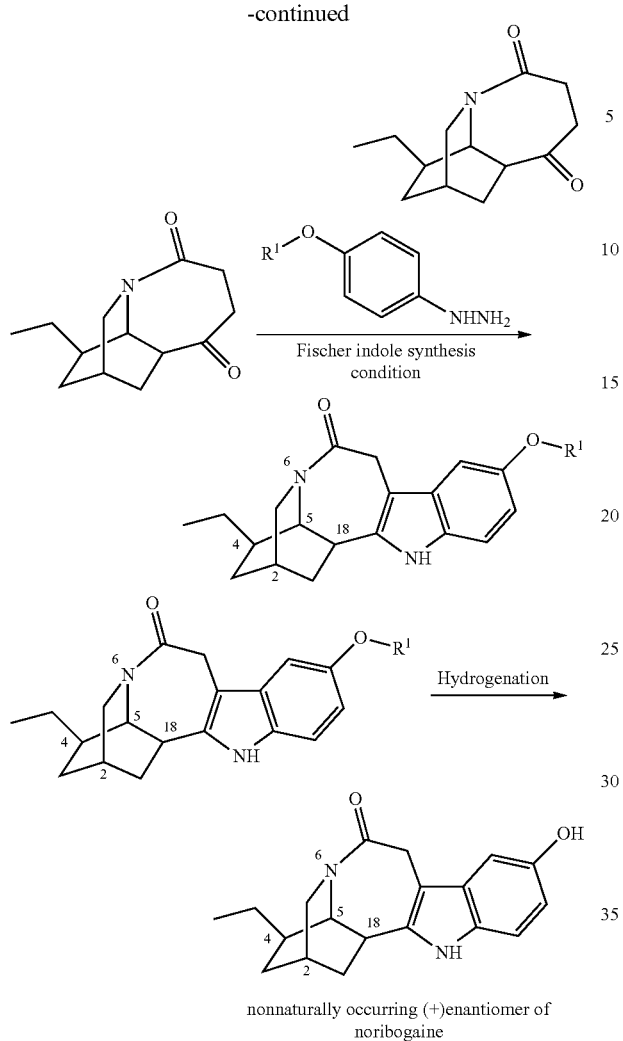

Thus, in one embodiment, this invention provides a process for preparing a compound of formula:

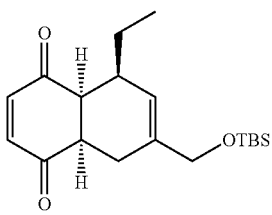 [SMILES: CC[C@H]1C=C(CO[Si](C)(C)C(C)(C)C)C[C@H]2C(=O)C=CC(=O)[C@@H]12]

comprising contacting benzoquinone with a diene compound of formula:

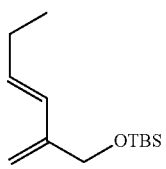

and a Ti((S)-binol)Cl$_2$ catalyst under conditions to provide the compound of formula:

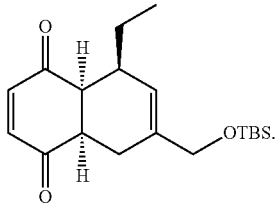 [SMILES: CC[C@H]1C=C(CO[Si](C)(C)C(C)(C)C)C[C@H]2C(=O)C=CC(=O)[C@@H]12]

It is contemplated that other silicon protecting group such as TIPS, TBDMS, or triphenyl silyl can be reasonably used in place of TBS. Benzoquinone is combined with, e.g., at least an equimolar amount of the diene in an inert chlorinated solvent in presence of a catalytic amount, preferably 20%-35% molar amount, still more preferably, 25%-30% molar amount with respect to benzoquinone, of Ti((S)-binol)Cl$_2$. The concentration of the reactants and the catalyst in the reaction solvent are as follows: benzoquinone, 0.05-0.2 molar, preferably 0.09-0.13 molar, still more preferably 0.11 molar: diene, 0.05-0.2 molar, preferably 0.1-0.14 molar, still more preferably 0.12 molar; and the catalyst, 0.01-0.1 molar, preferably 0.02-0.06 molar, still more preferably 0.03 molar. The reaction is performed at room temperature for a period of time sufficient to effect a substantial completion of the reaction.

While performing the above reaction under the conditions described, it was surprisingly observed that the desired enantiomer was obtained in 96% ee. Such a high ee allows the reaction to be used for manufacturing highly enantiomerically pure noribogaine suitable for human administration at reasonable manufacturing costs. The ee obtained for this reaction surpasses the 87% ee reported by White et al., *Helv. Chim. Acta*, Vol. 85 (2002), 4306-4327 (White), and incorporated herein in its entirety by reference. In White, despite optimization, a higher ee was not obtained. See, White at page 4314. An 87% ee corresponds to 93.5% of the major enantiomer. A process with 87% ee is undesirable from a manufacturing standpoint because it lowers chemical yield of the desired enantiomer, and adds one or more extra steps to separate the desired enantiomer from the undesired enantiomer. However, it is well known that when the ee excess is already around 87% after substantial optimization, it is challenging to improve it further. Under the conditions White reported, toluene was used as the reaction solvent and the following concentrations of the reactants and the catalyst were used: benzoquinone (0.83 molar), diene (0.97 molar), and catalyst (0.25 molar). Furthermore, according to White, 4 angstrom molecular sieves used during in situ preparation of the catalyst was removed by centrifugation.

Therefore it was surprising that in the above reaction, when dichloromethane was used in place of toluene, the concentrations of the reactants and the catalyst were reduced by about 7 fold, and the molecular sieves used for preparing the catalyst were filtered off instead of being removed by centrifugation, the ee of the diene obtained increased to 96%. Or in other words, the reaction produced 98% of the desired enantiomer.

In another embodiment, this invention provides a process for preparing a compound of formula:

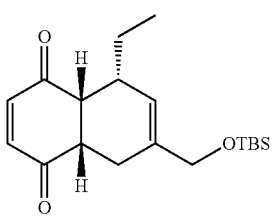 [SMILES: CC[C@@H]1C=C(CO[Si](C)(C)C(C)(C)C)C[C@@H]2C(=O)C=CC(=O)[C@@H]21]

comprising contacting benzoquinone with a diene compound of formula:

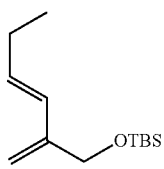

and a Ti((R)-binol)Cl$_2$ catalyst under Diels Alder reaction conditions to provide the compound of formula:

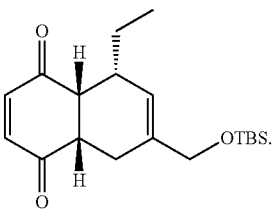 [SMILES: CC[C@@H]1C=C(CO[Si](C)(C)C(C)(C)C)C[C@@H]2C(=O)C=CC(=O)[C@@H]21]

It is contemplated that another silicon protecting group be reasonably used in place of OTBS. Preferred reaction conditions for this reaction are the same as those described above for the Diels Alder reaction using a Ti((S)-binol)Cl$_2$ catalyst. Ti((R)-binol)Cl$_2$ or Ti((S)-binol)Cl$_2$ is preferably prepared in situ by reacting (R) or (S)-binol with Ti(—OCHMe$_2$)$_2$Cl$_2$.

In another embodiment, this invention provides a process for preparing a compound of formula:

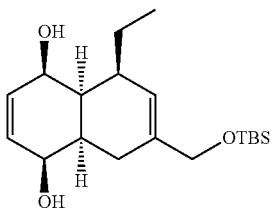 [SMILES: CC[C@H]1C=C(CO[Si](C)(C)C(C)(C)C)C[C@@H]2[C@H]1[C@H](O)C=C[C@@H]2O]

comprising contacting the compound of formula:

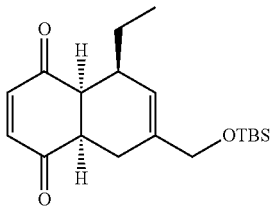 [SMILES: CC[C@H]1C=C(CO[Si](C)(C)C(C)(C)C)C[C@H]2C(=O)C=CC(=O)[C@@H]12]

with a reducing agent under conditions to provide the compound of formula:

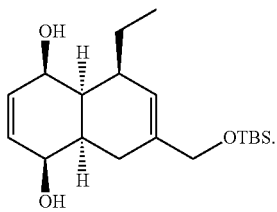 [SMILES: CC[C@H]1C=C(CO[Si](C)(C)C(C)(C)C)C[C@@H]2[C@H]1[C@H](O)C=C[C@@H]2O]

In a preferred embodiment, the reducing agent is diisobutylaluminum hydride.

In another embodiment, this invention provides a process for preparing a compound of formula:

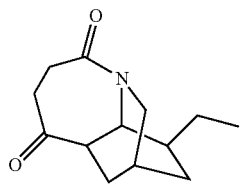 [SMILES: CCC1CC2CC3C(=O)CCC(=O)N(C2)C13]

comprising the steps of:
(i) contacting the compound of formula

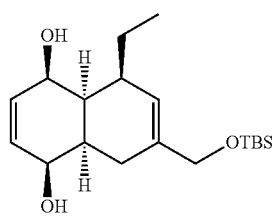 [SMILES: CC[C@H]1C=C(CO[Si](C)(C)C(C)(C)C)C[C@@H]2[C@H]1[C@H](O)C=C[C@@H]2O]

under hydrogenation conditions to provide a compound of formula

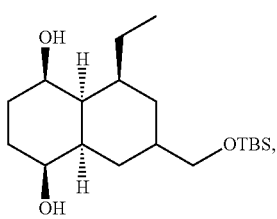 [SMILES: CC[C@H]1CC(CO[Si](C)(C)C(C)(C)C)C[C@@H]2[C@H]1[C@H](O)CC[C@@H]2O]

(ii) contacting the compound of formula:

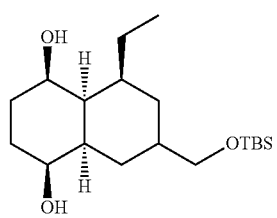 [SMILES: CC[C@H]1CC(CO[Si](C)(C)C(C)(C)C)C[C@@H]2[C@H]1[C@H](O)CC[C@@H]2O]

with an oxidizing agent under conditions to provide a compound of formula:

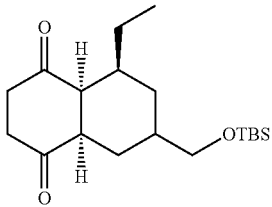 [SMILES: CC[C@H]1CC(CO[Si](C)(C)C(C)(C)C)C[C@H]2C(=O)CCC(=O)[C@@H]12]

(iii) contacting the compound of formula:

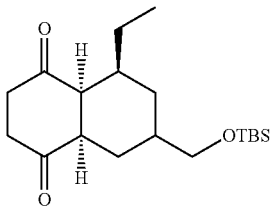 [SMILES: CC[C@H]1CC(CO[Si](C)(C)C(C)(C)C)C[C@H]2C(=O)CCC(=O)[C@@H]12]

with methanol and pyridinium para toluene sulfonate to provide a compound of formula:

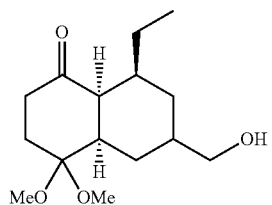 [SMILES: CC[C@H]1CC(CO)C[C@@H]2[C@H]1C(=O)CCC2(OC)OC]

(iv) contacting the compound of formula:

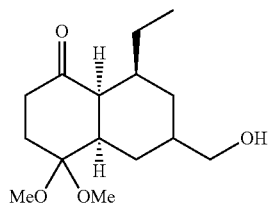 [SMILES: CC[C@H]1CC(CO)C[C@@H]2[C@H]1C(=O)CCC2(OC)OC]

with triisopropyl silyl chloride and imidazole to provide the compound of formula:

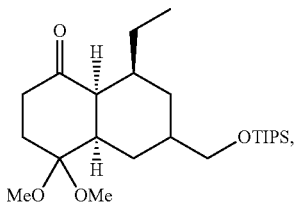

(v) contacting the compound of formula:

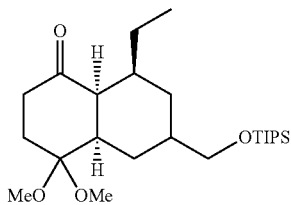

with a salt of $NH_2OH$ and a base to provide the compound of formula:

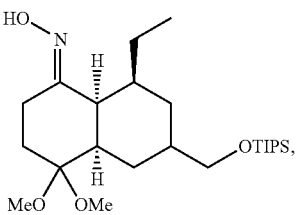

(vi) contacting the compound of formula

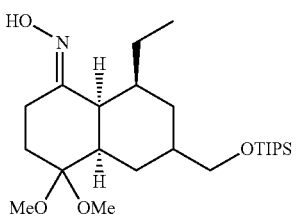

with $R^sSO_2Cl$ wherein $R^s$ is alkyl, fluoroalkyl, aryl, or aryl substituted with an alkyl or a halogen group, a base, and optionally a nucleophilic catalyst such as 4-N,N-dialkylaminopyridine to provide a compound of formula:

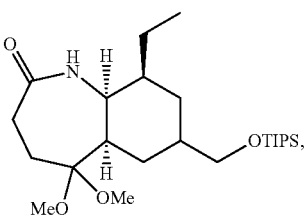

(vii) contacting the compound of formula:

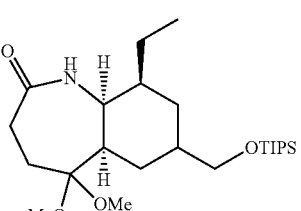

with fluoride anion to provide the compound of formula:

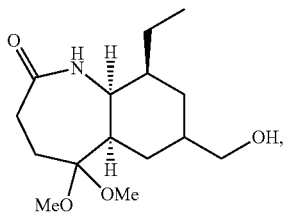 [SMILES: CC[C@H]1CC(CO)C[C@@H]2[C@H]1NC(=O)CCC2(OC)OC]

(viii) contacting the compound of formula:

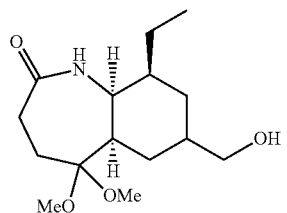 [SMILES: CC[C@H]1CC(CO)C[C@@H]2[C@H]1NC(=O)CCC2(OC)OC]

with R$^s$SO$_2$Cl wherein R$^s$ is alkyl, fluoroalkyl, aryl, or aryl substituted with an alkyl or a halogen group, a base, and optionally a 4-N,N-dialkylaminopyridine to provide a compound of formula:

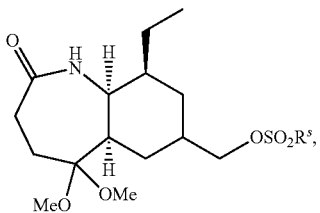

(ix) contacting the compound of formula:

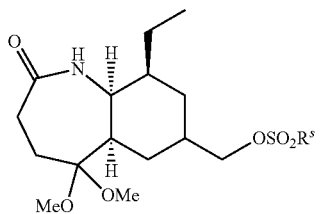

with a non nucleophilic base to provide a compound of formula:

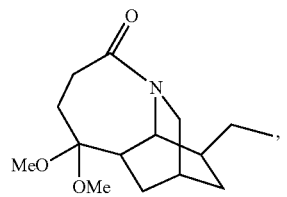 [SMILES: CCC1CC2CC3C1N(C2)C(=O)CCC3(OC)OC]

and (x) contacting the compound of formula:

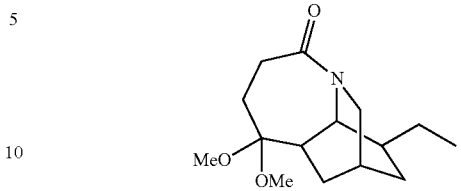

with an acid to provide the compound of formula:

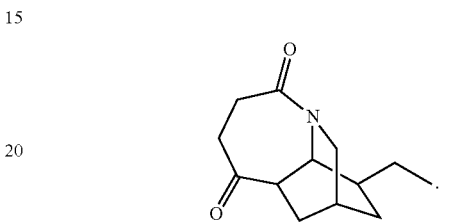

Steps (i) to (x) can be performed substantially according to the methods described in White, supra. In step (i), the hydrogenation is performed preferably employing a catalyst such Rh/Al$_2$O$_3$ and hydrogen, which catalyst does not produce substantial amounts of the hydrogenolyzed product. Upon hydrogenolysis, the allylic hydroxy group(s) can be replaced by hydrogen atom(s). A variety of oxidizing agents can be employed for step (ii) such as for example pyridinum dichromate, pyridinium chlorochromate, and the like. Those oxidizing agents are preferred that would not convert the tributylsilyloxy (OTBS) group to an —OH group. The selective ketalization of the less hindered ketone in step (iii) is performed using a mild acid catalyst such as pyridinium para toluene sulfonate (PPTS). In step (v), a salt of NH$_2$OH is reacted with the ketone and a base to provide the oxime. A variety of bases may be employed, including without limitation, acetates, preferably alkali metal acetates, alkali, and nitrogen containing bases such as pyridine, triethyl amine and the like. In step (vi), a variety of sulfonyl chlorides may be used, including without limitation para toluene sulfonyl chloride. In step (vi), a variety of bases may be employed, including without limitation, alkali and nitrogen containing bases such as pyridine, triethyl amine and the like. Preferred nucleophilic catalysts include 4-N,N-dimethylaminopyridine and 4-pyrrolidinopyridine. In step (vii) a variety of fluoride sources may be used including tertiary alkyl ammonium fluorides, such a tetrabutylammonium fluoride. In step (viii), a variety of bases may be employed, including without limitation, alkali and nitrogen containing bases such as pyridine, triethyl amine and the like. Preferred nucleophilic catalysts include 4-N,N-dimethylaminopyridine and 4-pyrrolidinopyridine. In step (ix), preferred non-nucleophilic bases used include, hydrides such as sodium, potassium and calcium hydrides. In step (x), a variety of acids can be used to convert the dimethyl ketal to the ketone. These reactions are carried out in solvents that are inert under the reaction conditions. The reactions are carried out for a time sufficient to provide substantial amount of the desired product. The reactions are monitored by thin layer chromatography. Depending on the amount of impurity present, a product may be separated by column chromatography, crystallization, or such other techniques well known to the skilled artisan, or the reaction product may be used without further purification in the next step.

In another embodiment, this invention provides a process for converting:

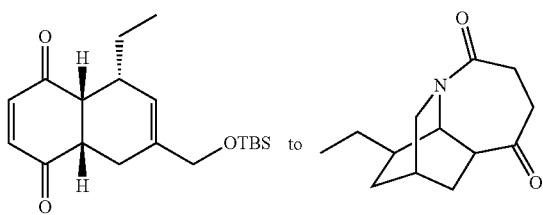 [SMILES: CC[C@@H]1C=C(CO[Si](C)(C)C(C)(C)C)C[C@@H]2C(=O)C=CC(=O)[C@@H]21 ; CCC1CC2CC3C(=O)CCC(=O)N(C2)C13]

following the process provided hereinabove for synthesizing:

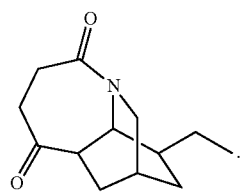 [SMILES: CCC1CC2CC3C(=O)CCC(=O)N(C2)C13]

In another embodiment, this invention provides a process for preparing a compound of formula:

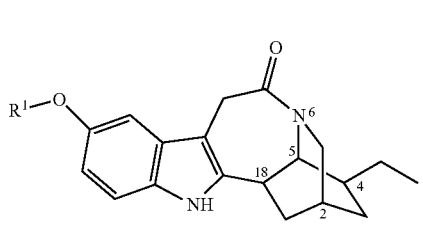

comprising contacting a ketoamide compound of formula:

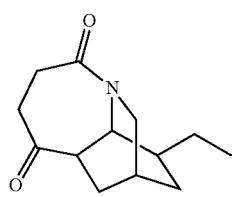 [SMILES: CCC1CC2CC3C(=O)CCC(=O)N(C2)C13]

with a substituted phenyl hydrazine of formula:

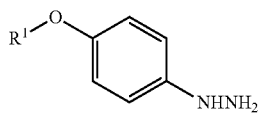

or a salt thereof, wherein $R^1$ is $C_1$-$C_4$ alkyl optionally substituted with 1-3 phenyl or substituted phenyl groups, wherein the substituted phenyl is substituted with 1-3 $C_1$-$C_4$ alkyl or $C_1$-$C_4$ alkoxy groups, under Fischer indole synthesis conditions to provide the keto ibogaine derivative of formula:

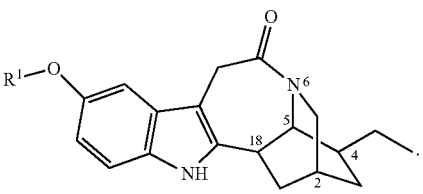

In another embodiment, $R^1$ is methyl. In another embodiment, $R^1$ is a methyl group substituted with 1-3, preferably 1-2, more preferably 1 phenyl group, which phenyl group is optionally substituted with 1-3 $C_1$-$C_4$ alkyl or $C_1$-$C_4$ alkoxy groups. In another embodiment, $R^1$ is benzyl. When $R^1$ is methyl, it is preferred to not use a boron based Lewis acid, such as $BF_3$ etherate, for this transformation.

In another embodiment, the ketoamide compound is present at least 80%, preferably at least 90%, more preferably at least 95%, or still more preferably at least 98% as the (5aR,7R,9S,9aS)-9-ethyl-3,4,5a,6,7,8,9,9a-octahydro-1,7-methano-1H-benz[b]azepine-2,5-dione enantiomer:

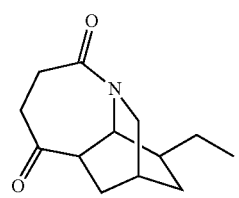 [SMILES: CCC1CC2CC3C(=O)CCC(=O)N(C2)C13]

In other words, the ketoamide compound contains, at least 60%, preferably at least 80%, more preferably at least 90%, or still more preferably at least 96% ee of the (5aR,7R,9S,9aS)-9-ethyl-3,4,5a,6,7,8,9,9a-octahydro-1,7-methano-1H-benz[b]azepine-2,5-dione enantiomer.

In another embodiment, the keto ibogaine derivative is present at least 80%, preferably at least 90%, more preferably at least 95%, or still more preferably at least 98% as the 2(R), 4(S), 5(S), 6(S) and 18(R) enantiomer.

It is surprising that a substituted hydrazine containing an electron donating 4-alkoxy substituent effectively provides the tricyclic indole under Fischer indole synthesis conditions. The ketoamide compound is combined with at least an equimolar amount of the substituted phenylhydrazine or a salt thereof, in the presence of an acid or a mixture of acids. Suitable acids include carboxylic Bronsted acids such as acetic acid and Lewis acids such as $BF_3$ and its solvates such as etherates. The reaction is performed at 40° C.-60° C., and may optionally be warmed up to 70° C.-90° C., for a period of time sufficient to effect a substantial completion of the reaction. Suitable solvent include acetic acid, propionic acid and the like. Suitable salts of the substituted phenylhydrazine include salts of mineral acids, such as HCl.

In another embodiment, this invention provides a method of synthesis comprising contacting a ketoamide compound of formula:

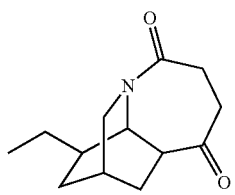 [SMILES: CCC1CC2CC3C(=O)CCC(=O)N(C2)C13]

with a substituted phenyl hydrazine of formula:

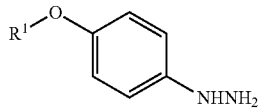

or a salt thereof, wherein $R^1$ is $C_1$-$C_4$ alkyl optionally substituted with 1-3 phenyl or substituted phenyl groups, wherein the substituted phenyl is substituted with 1-3 $C_1$-$C_4$ alkyl or $C_1$-$C_4$ alkoxy groups, under Fischer indole synthesis conditions to provide a keto ibogaine derivative of formula:

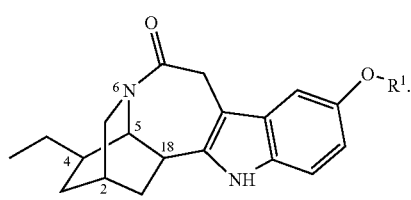

In another embodiment, the ketoamide compound is present at least 80%, preferably at least 90%, more preferably at least 95%, or still more preferably at least 98% as the (5aS,7S,9R,9aR)-9-ethyl-3,4,5a,6,7,8,9,9a-octahydro-1,7-methano-1H-benz[b]azepine-2,5-dione enantiomer:

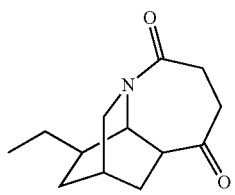 [SMILES: CCC1CC2CC3C(=O)CCC(=O)N(C2)C13]

In another embodiment, the keto ibogaine derivative is present at least 80%, preferably at least 90%, more preferably at least 95%, or still more preferably at least 98% as the 2(S), 4(R), 5(R), 6(R) and 18(S) enantiomer.

In another embodiment, the process further comprises subjecting the keto ibogaine derivative:

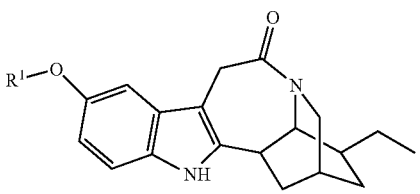

under amide reduction conditions to provide ibogaine or the derivative thereof of formula:

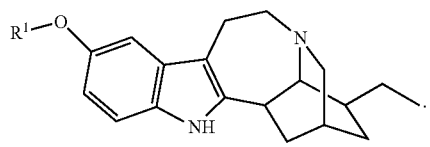

The keto ibogaine derivative is contacted with at least an equimolar, preferably 4-6 molar excess of a borohydride, preferably $NaBH_4$ and a Lewis acid, preferably, $BF_3$ etherate, in an inert solvent such as tetrahydrofuran. The reaction is performed initially at 0° C. and then at room temperature for a period of time sufficient to effect a substantial completion of the reaction.

In another embodiment, the process further comprises subjecting the keto ibogaine derivative:

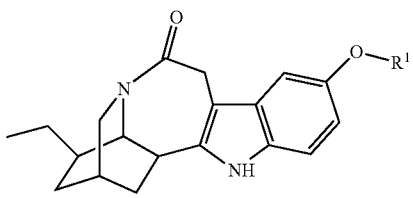

under amide reduction conditions to provide ibogaine or a derivative thereof of formula:

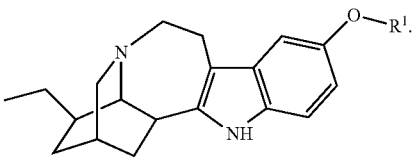

In another embodiment, the process further comprises deprotecting the compound of formula:

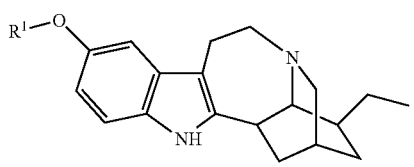

under deprotection conditions to provide naturally occurring (−) noribogaine:

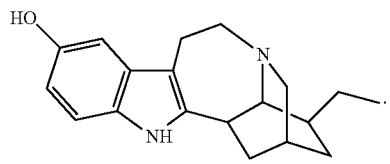 [SMILES: CCC1CC2CC3c4[nH]c5ccc(O)cc5c4CCN(C2)C13]

In another embodiment, the noribogaine obtained is present at least 80%, preferably at least 90%, more preferably at least 95%, or still more preferably at least 98% as the (−) or naturally occurring 2(R), 4(S), 5(S), 6(S) and 18(R) enantiomer of noribogaine. In another embodiment, $R^1$ is $C_1$-$C_4$ alkyl, and the deprotection is performed by using BBr₃ in an inert solvent under conditions well known to the skilled artisan. In another embodiment, R¹ is benzyl and the deprotection is performed by using hydrogenolysis or catalytic hydrogenation conditions.

In another embodiment, the process further comprises deprotecting the compound of formula:

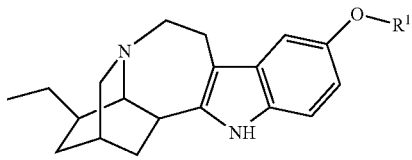

under deprotection conditions to provide noribogaine:

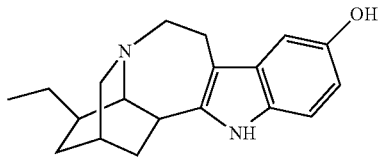 [SMILES: CCC1CC2CC3c4[nH]c5ccc(O)cc5c4CCN(C2)C13]

or a salt thereof.

In another embodiment, the noribogaine obtained is present at least 80%, preferably at least 90%, more preferably at least 95%, or still more preferably at least 98% as the (+) or nonnatural 2(S), 4(R), 5(R), 6(R) and 18(S) enantiomer of noribogaine.

In another aspect, this invention provides (−) noribogaine and (+)noribogaine, and intermediates thereto, preferably in substantially enantiomerically pure forms, prepared according to the processes provided herein.

UTILITY

The indole isoquinuclidene derivative (−) noribogaine has utility in the treatment of drug dependency and as an analgesic. See U.S. Pat. Nos. 6,348,456 7,220,737, supra. The indole and benzofuran fused isoquinuclidene derivatives provided and (+) noribogaine herein have utility to test their interaction with the opioid receptors to better understand the mechanism of (−) noribogaine's analgesic action. The novel compounds provided herein also have utility as intermediates to synthetic noribogaine or as compounds having activity in drug dependency or as analgesics.

The invention claimed is:

1. A compound of Formula (I-i) or (VI-i):

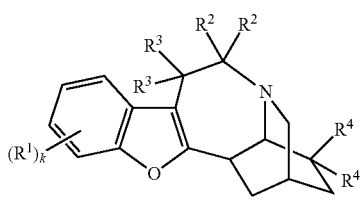

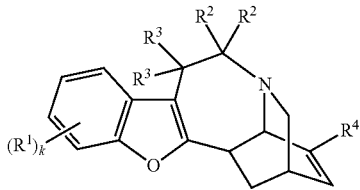

or a salt or enantiomer thereof wherein
k is 1, 2, or 3;
each R¹ is independently selected from the group consisting of hydrogen, halo, amino, hydroxy, $C_1$-$C_6$ alkoxy, $C_1$-$C_6$ alkyl, $C_2$-$C_6$ alkenyl, $C_2$-$C_6$ alkynyl, cyano, nitro, —$N_3$, and —$CO_2H$ or an ester thereof, wherein the alkyl, alkoxy, alkenyl, or the alkynyl group is optionally substituted with 1-3 substituents selected from the group consisting of keto, halo, amino, hydroxy, cyano, nitro, —$N_3$, phenyl optionally substituted with 1-3 substituents selected from the group consisting of $C_1$-$C_6$ alkyl and $C_1$-$C_6$ alkoxy, and —$CO_2H$ or an ester thereof;
$R^2$ is hydrogen or $C(R^2)_2$ is a keto group;
$R^3$ is selected from the group consisting of hydrogen, halo, $C_1$-$C_6$ alkyl, $C_2$-$C_6$ alkenyl, $C_2$-$C_6$ alkynyl, wherein the alkyl, alkenyl, or the alkynyl group is optionally substituted with 1-3 substituents selected from the group consisting of keto, halo, amino, hydroxy, cyano, nitro, —$N_3$, and —$CO_2H$ or an ester thereof;
each $R^4$ independently is selected from the group consisting of hydrogen, hydroxy, —$SR^{41}$, —$OR^{42}$, $C_1$-$C_6$ alkyl, $C_2$-$C_6$ alkenyl, and $C_2$-$C_6$ alkynyl, wherein the alkyl, alkenyl, or the alkynyl group is optionally substituted with 1-3 substituents selected from the group consisting of, halo, $C_1$-$C_6$ alkoxy, amino, hydroxy, cyano, nitro, —$NHCOCH_3$, and —$N_3$, or the 2 $R^4$ groups together with the carbon atom to which they are bonded to form a keto (C=O) group, a Schiff base (=$NR^{43}$), a vinylidene moiety of formula =$CR^{48}R^{49}$, or form a cyclic ketal or thioketal, which cyclic ketal or thioketal is of formula:

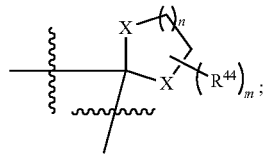

each $R^{41}$ is independently selected from the group consisting of $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof, $C_2$-$C_6$ alkenyl, $C_2$-$C_6$ alkynyl, $C_6$-$C_{10}$ aryl, $C_2$-$C_{10}$ heteroaryl, $C_3$-$C_8$ cycloalkyl, and $C_3$-$C_8$ heterocyclyl;
each $R^{42}$ is independently selected from the group consisting of $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof, $C_2$-$C_6$ alkenyl, and $C_2$-$C_6$ alkynyl;
where X in both occurrences is either oxygen or sulfur;

m is 1, 2, 3, or 4;
n is 1 or 2;
$R^{43}$ is selected from the group consisting of $C_6$-$C_{10}$ aryl and $C_2$-$C_{10}$ heteroaryl;
$R^{44}$ is selected from the group consisting of $C_1$-$C_6$ alkyl and $C_6$-$C_{10}$ aryl;
$R^{48}$ is hydrogen, $C_1$-$C_6$ alkyl, $C_2$-$C_6$ alkenyl, and $C_2$-$C_6$ alkynyl, wherein the alkyl, alkenyl, or the alkynyl group is optionally substituted with 1-3 substituents selected from the group consisting of keto, $C_1$-$C_6$ alkoxy, amino, hydroxy, cyano, nitro, —NHCOCH$_3$, and —CO$_2$H or an ester thereof; and
$R^{49}$ is hydrogen or $C_1$-$C_6$ alkyl.

2. The compound of claim 1, of (IB):

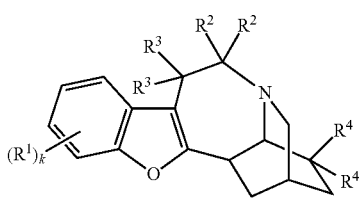

(IB)

wherein k and $R^1$, $R^2$, $R^3$, and $R^4$ are defined as in claim 1.

3. The compound of claim 1, of Formula (IIB):

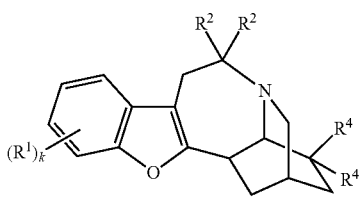

(IIB)

wherein k and $R^1$, $R^2$, and $R^4$ are defined as in claim 1.

4. The compound of claim 1, of Formula (IIIB):

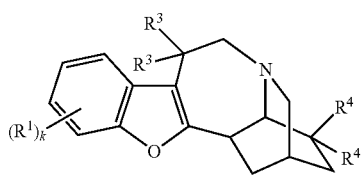

(IIIB)

wherein k and $R^1$, $R^3$, and $R^4$ are defined as in claim 1.

5. A compound of Formula (IVB):

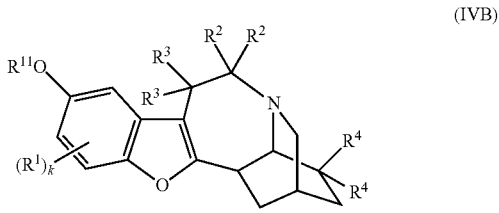

(IVB)

wherein $R^{11}$ is selected from the group consisting of hydrogen and $C_1$-$C_6$ alkyl optionally substituted with 1-3 substituents selected from the group consisting of halo, amino, hydroxy, cyano, nitro, —N$_3$, and —CO$_2$H or an ester thereof, and phenyl optionally substituted with 1-3 substituents selected from the group consisting of $C_1$-$C_6$ alkyl and $C_1$-$C_6$ alkoxy;
k is 1 or 2;
and $R^1$, $R^2$, $R^3$, and $R^4$ are defined as in claim 1.

6. A compound of Formula (IVD) or (VIB):

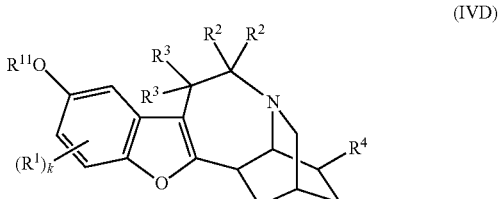

(IVD)

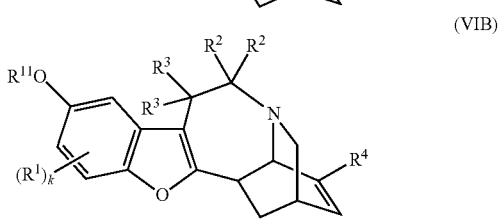

(VIB)

wherein $R^{11}$ is selected from the group consisting of hydrogen and $C_1$-$C_6$ alkyl optionally substituted with 1-3 substituents selected from the group consisting of halo, amino, hydroxy, cyano, nitro, —N$_3$, and —CO$_2$H or an ester thereof, and phenyl optionally substituted with 1-3 substituents selected from the group consisting of $C_1$-$C_6$ alkyl and $C_1$-$C_6$ alkoxy;
k is 1 or 2;
and $R^1$, $R^2$, $R^3$, and $R^4$ are defined as in claim 1.

7. An isolated enantiomer of a compound of claim 1 in substantial enantiomeric excess.

* * * * *